United States Patent
Adler et al.

(10) Patent No.: US 9,610,064 B2
(45) Date of Patent: Apr. 4, 2017

(54) MULTIMODAL IMAGING SYSTEM, APPARATUS, AND METHODS

(76) Inventors: Desmond Adler, Melrose, MA (US); Joseph M. Schmitt, Andover, MA (US); Mattias Dahlberg, Uppsala (SE); Par Gustafsson, Uppsala (SE); Ulrik Hubinette, Alunda (SE); Magnus Samuelsson, Uppsala (SE); Johan Svanerudh, Uppsala (SE)

(*) Notice: Subject to any disclaimer, the term of this patent is extended or adjusted under 35 U.S.C. 154(b) by 0 days.

(21) Appl. No.: 13/484,763

(22) Filed: May 31, 2012

(65) Prior Publication Data
US 2012/0310081 A1 Dec. 6, 2012

Related U.S. Application Data

(60) Provisional application No. 61/491,701, filed on May 31, 2011, provisional application No. 61/555,663, filed on Nov. 4, 2011.

(51) Int. Cl.
*A61B 5/05* (2006.01)
*A61B 8/00* (2006.01)
(Continued)

(52) U.S. Cl.
CPC .............. *A61B 8/54* (2013.01); *A61B 5/0035* (2013.01); *A61B 5/0084* (2013.01);
(Continued)

(58) Field of Classification Search
USPC .................. 600/427, 478; 356/451, 496, 479
See application file for complete search history.

(56) References Cited

U.S. PATENT DOCUMENTS 4,548,473 A    10/1985    Lo et al.
5,140,975 A *    8/1992    Krauter ........................ 600/139
(Continued)

FOREIGN PATENT DOCUMENTS

JP     63127201     5/1988
JP     03-92143     4/1991
(Continued)

OTHER PUBLICATIONS

English Translation of Japanese Office Action for Application No. JP 2012-124251, dated Dec. 10, 2013, 3 pages.
(Continued)

*Primary Examiner* — Joel F Brutus
(74) *Attorney, Agent, or Firm* — K&L Gates LLP

(57) ABSTRACT

In part, the invention relates to an image data collection system. The system can include an interferometer having a reference arm that includes a first optical fiber of length of L1 and a sample arm that includes a second optical fiber of length of L2 and a first rotary coupler configured to interface with an optical tomography imaging probe, wherein the rotary coupler is in optical communication with the sample arm. In one embodiment, L2 is greater than about 5 meters. The first optical fiber and the second optical fiber can both be disposed in a common protective sheath. In one embodiment, the system further includes an optical element configured to adjust the optical path length of the reference arm, wherein the optical element is in optical communication with the reference arm and wherein the optical element is transmissive or reflective.

24 Claims, 23 Drawing Sheets

(51) Int. Cl.
*A61B 5/00* (2006.01)
*A61B 5/0215* (2006.01)
*A61B 8/12* (2006.01)
*A61B 6/00* (2006.01)
*A61B 8/08* (2006.01)

(52) U.S. Cl.
CPC .......... *A61B 5/0215* (2013.01); *A61B 5/6852* (2013.01); *A61B 8/12* (2013.01); *A61B 8/4416* (2013.01); *A61B 8/5261* (2013.01); *A61B 5/0044* (2013.01); *A61B 5/0046* (2013.01); *A61B 5/0066* (2013.01); *A61B 6/504* (2013.01); *A61B 6/5247* (2013.01); *A61B 8/0891* (2013.01); *A61B 8/4433* (2013.01); *A61B 2560/045* (2013.01); *A61B 2560/0437* (2013.01); *A61B 2560/0456* (2013.01)

(56) References Cited

U.S. PATENT DOCUMENTS

| | | | |
|---|---|---|---|
| 5,321,501 A | 6/1994 | Swanson et al. | |
| 5,459,570 A | 10/1995 | Swanson et al. | |
| 5,465,147 A | 11/1995 | Swanson | |
| 5,509,093 A | 4/1996 | Miller et al. | |
| 5,518,810 A | 5/1996 | Nishihara et al. | |
| 5,619,368 A | 4/1997 | Swanson | |
| 5,632,767 A | 5/1997 | Sinofsky | |
| 5,643,253 A | 7/1997 | Baxter et al. | |
| 5,748,598 A | 5/1998 | Swanson et al. | |
| 5,784,352 A | 7/1998 | Swanson et al. | |
| 5,908,415 A | 6/1999 | Sinofsky | |
| 5,947,959 A | 9/1999 | Sinofsky | |
| 5,949,491 A * | 9/1999 | Callahan et al. | 348/442 |
| 5,956,355 A | 9/1999 | Swanson et al. | |
| 6,111,645 A | 8/2000 | Tearney et al. | |
| 6,134,003 A | 10/2000 | Tearney et al. | |
| 6,160,826 A | 12/2000 | Swanson et al. | |
| 6,179,611 B1 * | 1/2001 | Everett et al. | 433/29 |
| 6,191,862 B1 | 2/2001 | Swanson et al. | |
| 6,270,492 B1 | 8/2001 | Sinofsky | |
| 6,282,011 B1 | 8/2001 | Tearney et al. | |
| 6,348,960 B1 | 2/2002 | Etori et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,564,089 B2 | 5/2003 | Izatt et al. | |
| 6,570,659 B2 | 5/2003 | Schmitt | |
| 6,673,015 B1 | 1/2004 | Glover et al. | |
| 6,692,824 B2 | 2/2004 | Benz et al. | |
| 6,706,004 B2 | 3/2004 | Tearney et al. | |
| 6,718,089 B2 | 4/2004 | James et al. | |
| 6,760,112 B2 | 7/2004 | Reed et al. | |
| 6,769,307 B1 * | 8/2004 | Dixon et al. | 73/602 |
| 6,879,851 B2 | 4/2005 | McNamara et al. | |
| 6,891,984 B2 | 5/2005 | Petersen et al. | |
| 6,932,809 B2 | 8/2005 | Sinofsky | |
| 6,942,657 B2 | 9/2005 | Sinofsky et al. | |
| 6,974,557 B1 | 12/2005 | Webler et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,298,478 B2 | 11/2007 | Gilbert et al. | |
| 7,355,699 B2 | 4/2008 | Gilbert et al. | |
| 7,408,648 B2 | 8/2008 | Kleen et al. | |
| 7,412,141 B2 | 8/2008 | Gowda et al. | |
| 7,414,779 B2 | 8/2008 | Huber et al. | |
| 7,415,049 B2 | 8/2008 | Flanders et al. | |
| 7,492,522 B2 | 2/2009 | Gilbert et al. | |
| 7,576,861 B2 | 8/2009 | Gilbert et al. | |
| 7,625,366 B2 | 12/2009 | Atlas | |
| 7,711,413 B2 | 5/2010 | Feldman et al. | |
| 7,783,337 B2 | 8/2010 | Feldman et al. | |
| 7,813,609 B2 | 10/2010 | Petersen et al. | |
| 7,848,791 B2 | 12/2010 | Schmitt et al. | |
| 7,853,316 B2 | 12/2010 | Milner et al. | |
| 7,916,387 B2 | 3/2011 | Schmitt et al. | |
| 7,935,060 B2 | 5/2011 | Schmitt et al. | |
| 7,967,743 B2 | 6/2011 | Ishihara | |
| 8,358,461 B2 | 1/2013 | Huber et al. | |
| 8,503,844 B2 | 8/2013 | Petersen et al. | |
| 2002/0147394 A1 * | 10/2002 | Ellingsen | 600/410 |
| 2002/0161351 A1 | 10/2002 | Samson et al. | |
| 2003/0004412 A1 * | 1/2003 | Izatt et al. | 600/425 |
| 2004/0176920 A1 * | 9/2004 | Monfared et al. | 702/75 |
| 2004/0228630 A1 * | 11/2004 | Kim et al. | 398/83 |
| 2005/0094099 A1 | 5/2005 | Newman et al. | |
| 2005/0201662 A1 | 9/2005 | Petersen et al. | |
| 2005/0203338 A1 | 9/2005 | Couvillon, Jr. et al. | |
| 2006/0094982 A1 | 5/2006 | Corl et al. | |
| 2006/0095065 A1 | 5/2006 | Tanimura et al. | |
| 2006/0279742 A1 * | 12/2006 | Tearney et al. | 356/498 |
| 2007/0232933 A1 | 10/2007 | Gille et al. | |
| 2007/0278389 A1 * | 12/2007 | Ajgaonkar et al. | 250/221 |
| 2008/0043243 A1 * | 2/2008 | Lee et al. | 356/477 |
| 2008/0097185 A1 * | 4/2008 | Feldman et al. | 600/407 |
| 2008/0117427 A1 | 5/2008 | Teramura et al. | |
| 2008/0118886 A1 * | 5/2008 | Liang et al. | 433/29 |
| 2008/0177183 A1 * | 7/2008 | Courtney et al. | 600/463 |
| 2009/0131800 A1 * | 5/2009 | Liang | 600/476 |
| 2009/0174931 A1 | 7/2009 | Huber et al. | |
| 2009/0195514 A1 | 8/2009 | Glynn et al. | |
| 2009/0284749 A1 * | 11/2009 | Johnson et al. | 356/497 |
| 2009/0306520 A1 | 12/2009 | Schmitt et al. | |
| 2010/0076320 A1 | 3/2010 | Petersen et al. | |
| 2010/0094127 A1 | 4/2010 | Xu | |
| 2010/0110377 A1 * | 5/2010 | Maloca et al. | 351/208 |
| 2010/0135111 A1 * | 6/2010 | Bates et al. | 367/11 |
| 2010/0220334 A1 * | 9/2010 | Condit et al. | 356/497 |
| 2010/0253949 A1 | 10/2010 | Adler et al. | |
| 2011/0007315 A1 | 1/2011 | Petersen et al. | |
| 2011/0071404 A1 | 3/2011 | Schmitt et al. | |
| 2011/0071405 A1 | 3/2011 | Judell et al. | |
| 2011/0101207 A1 | 5/2011 | Schmitt | |
| 2011/0151980 A1 | 6/2011 | Petroff | |
| 2011/0157686 A1 | 6/2011 | Huber et al. | |
| 2011/0172511 A1 | 7/2011 | Schmitt et al. | |
| 2011/0178413 A1 | 7/2011 | Schmitt et al. | |
| 2011/0190586 A1 | 8/2011 | Kemp | |
| 2011/0216325 A1 | 9/2011 | Schmitt | |
| 2011/0228280 A1 | 9/2011 | Schmitt et al. | |
| 2011/0251497 A1 | 10/2011 | Corl et al. | |
| 2012/0162660 A1 | 6/2012 | Kemp | |
| 2012/0165661 A1 | 6/2012 | Kemp et al. | |
| 2012/0224751 A1 | 9/2012 | Kemp et al. | |
| 2012/0236883 A1 | 9/2012 | Adler | |
| 2012/0238869 A1 | 9/2012 | Schmitt et al. | |
| 2012/0250028 A1 | 10/2012 | Schmitt et al. | |
| 2012/0265077 A1 | 10/2012 | Gille et al. | |
| 2012/0310081 A1 | 12/2012 | Adler et al. | |
| 2013/0010303 A1 | 1/2013 | Petersen et al. | |
| 2013/0011034 A1 | 1/2013 | Glynn et al. | |
| 2013/0012811 A1 | 1/2013 | Schmitt et al. | |
| 2013/0015975 A1 | 1/2013 | Huennekens et al. | |
| 2013/0023761 A1 | 1/2013 | Petroff | |
| 2013/0023762 A1 | 1/2013 | Huennekens et al. | |
| 2013/0023763 A1 | 1/2013 | Huennekens et al. | |
| 2013/0030300 A1 | 1/2013 | Ahmed et al. | |
| 2013/0051728 A1 | 2/2013 | Petroff | |
| 2013/0072805 A1 | 3/2013 | Schmitt et al. | |
| 2013/0120296 A1 | 5/2013 | Merritt et al. | |
| 2013/0120297 A1 | 5/2013 | Merritt et al. | |
| 2013/0123616 A1 | 5/2013 | Merritt et al. | |
| 2013/0190633 A1 | 7/2013 | Dorando et al. | |

FOREIGN PATENT DOCUMENTS

| | | |
|---|---|---|
| JP | 07275222 | 10/1995 |
| JP | 08191794 | 7/1996 |
| JP | 11-113912 | 4/1999 |
| JP | 2005131393 | 5/2005 |

(56) References Cited

FOREIGN PATENT DOCUMENTS

| | | |
|---|---|---|
| JP | 2008-128708 | 5/2008 |
| WO | 2008089406 | 7/2008 |
| WO | 2009/137659 A1 | 11/2009 |
| WO | 2009140641 | 11/2009 |
| WO | 2010030882 | 3/2010 |
| WO | 2010044322 | 4/2010 |
| WO | 2011143387 | 11/2011 |
| WO | 2012087818 | 6/2012 |

OTHER PUBLICATIONS

International Preliminary Report on Patentability and Written Opinion of the International Searching Authority for International Application No. PCT/US2012/040060, mailed from the International Bureau on Dec. 12, 2013 (11 pages).

English translation of Japanese Office Action for Application No. JP-2012-124251, dated Sep. 30, 2014 (9 pages).

* cited by examiner

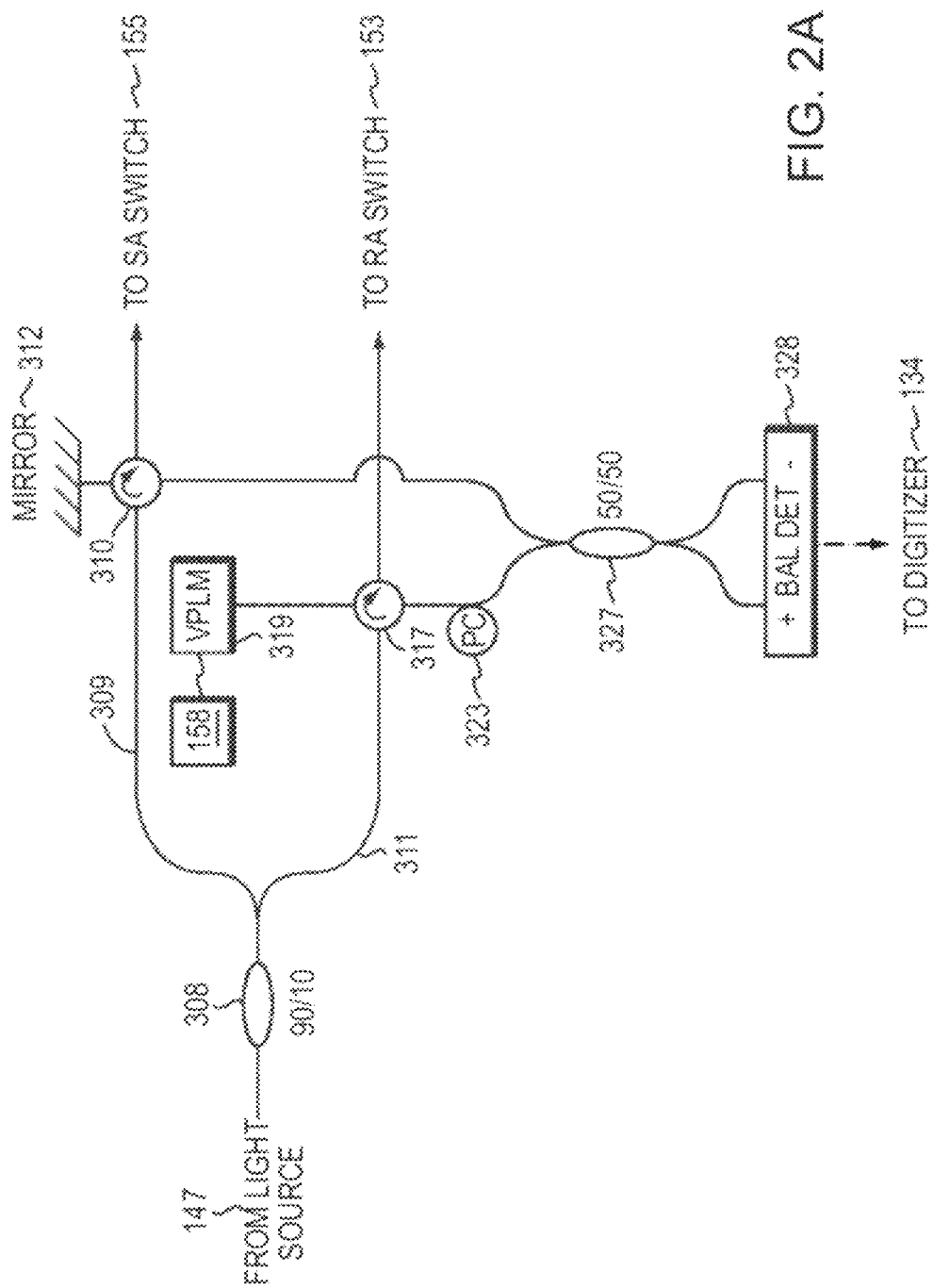

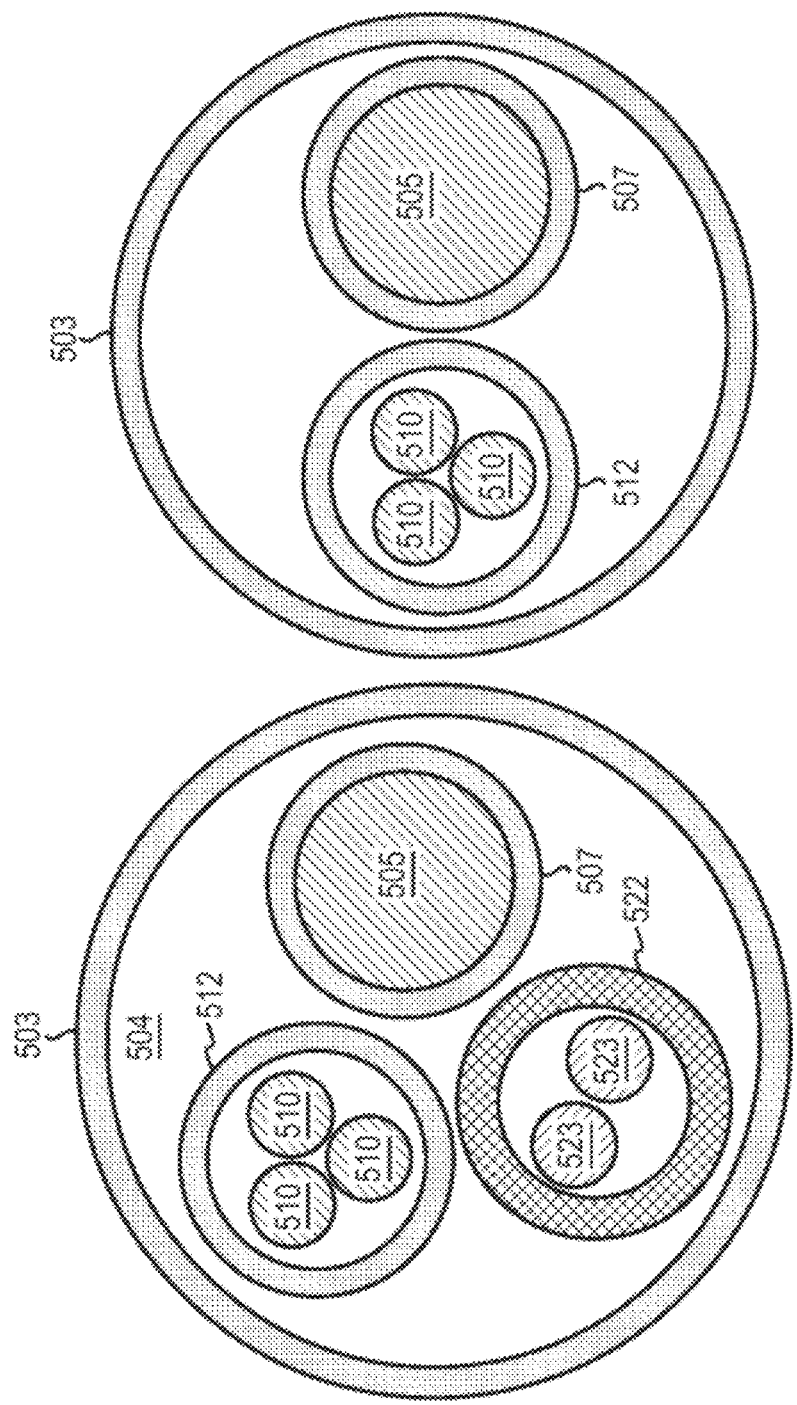

MULTIMODAL IMAGING SYSTEM, APPARATUS, AND METHODS

CROSS REFERENCE TO RELATED APPLICATIONS

This application claims priority to and the benefit of U.S. Provisional Patent Application No. 61/491,701, filed on May 31, 2011, and U.S. Provisional Patent Application No. 61/555,663, filed on Nov. 4, 2011, the disclosures of which are herein incorporated by reference in their entirety.

FIELD OF THE INVENTION

The invention relates generally to devices and methods suitable for use in the fields of medical treatment and diagnostics and more specifically to devices and methods that support one or more modes of data collection relevant to cardiology.

BACKGROUND

Interventional cardiologists incorporate a variety of diagnostic tools during catheterization procedures in order to plan, guide, and assess therapies. These tools typically include optical coherence tomography (OCT), intravascular ultrasound, (IVUS), fractional flow reserve (FFR), and angiography. Intravascular OCT, IVUS, and FFR are invasive catheter-based systems that collect optical, ultrasound, and pressure data, respectively, from inside blood vessels or with respect to a sample of interest. Angiography is a noninvasive x-ray imaging method that collects data from outside the body during injection of a radio-opaque contrast fluid.

Early OCT, IVUS, and FFR systems were typically single-purpose and incorporated only one of the three modalities. Each independent system was typically configured as a portable cart. If more than one modality was to be used during an interventional procedure, this approach had the significant disadvantage of increasing clutter in the catheterization lab and requiring time-consuming set-up procedures. More recently, diagnostic systems have begun to incorporate IVUS and FFR or OCT and FFR on the same console. "Integrated" IVUS and FFR systems have also been developed, where control devices and catheter interface devices are located in the procedure room, while data acquisition devices are located remotely in a control room. Such dual-modality, integrated systems reduce clutter and reduce the total cost for diagnostic equipment.

Unfortunately, existing integrated IVUS and FFR diagnostic systems suffer from various limitations that reduce their utility. One limitation is that existing integrated IVUS and FFR systems do not incorporate OCT imaging. OCT provides order-of-magnitude improvements to image resolution compared to IVUS. OCT also enables more accurate plaque characterization, quantitative lesion measurements, thrombus detection, visualization of stent malapposition and edge dissections, and assessment of stent coverage following implantation.

A second limitation is that existing integrated systems require a dedicated set of data acquisition and processing equipment to support each procedure room. This increases the capital costs associated with equipping multiple procedure rooms with diagnostic systems, leading to higher health care expenditures. This limitation is even more pronounced with OCT systems than with IVUS systems, since the optical and electronic hardware required for OCT imaging is significantly more expensive than that required for IVUS imaging.

Accordingly, a need therefore exists for a multimodal system and related devices that address these limitations.

SUMMARY OF THE INVENTION

The invention relates to a multimodal diagnostic system for use in interventional cardiology and other diagnostic fields. In one embodiment, multimodal or multiple modes refers to a plurality of data collection modalities. One aspect of the invention is a system that incorporates at least two of the following modalities in a single system: optical coherence tomography (OCT), intravascular ultrasound (IVUS), fractional flow reserve (FFR), and X-ray angiography measurements in a single system. A patient interface unit (PIU) can connect to one or more catheters to collect OCT and IVUS imaging data. FFR data collection can also be performed using wired or wireless pressure monitors and receivers. In one embodiment, angiographic x-ray images can be collected, stored, and/or routed using a computer or network. Such angiographic images can be co-registered with OCT and IVUS images obtained using the multimodal system.

The system modules can be distributed between a main control room, multiple satellite control rooms, multiple procedure rooms or within a room but remote from a common reference point such as a subject's or patient's location or a support they are disposed upon during a procedure. In one embodiment, a procedure room can be a catheterization lab (or cath lab), for example. In this way, ease of use is increased while hardware costs are decreased. In one embodiment, a probe, such as an OCT probe or an IVUS probe or an FFR probe is used in the procedure room to measure a sample of interest in a patient. Various network topologies, cable arrangements, and data routing techniques can be used to facilitate the operation of a given multimodal system.

In one aspect, the invention relates to a data collection system for acquiring data with respect to a patient disposed on a support. The system includes an imaging engine that includes an optical radiation source; an interferometer that includes a reference arm that includes a first optical fiber of length of L1 and a sample arm that includes a second optical fiber of length of L2; a patient interface unit configured to interface with a data collection probe, wherein the patient interface unit is in optical communication with the sample arm; and a display configured to display an image generated using optical coherence tomography data collected using the data collection probe, wherein the imaging engine is located remotely from the support, wherein the patient interface unit and the display are located proximal to the support.

In one embodiment, L2 is greater than about 5 meters. In one embodiment, the system includes a dock in optical communication with the patient interface unit. In one embodiment, the system further includes a protective sheath, wherein a section of the reference arm and a section of the sample arm between the imaging engine and the dock are at least partially disposed within the protective sheath such that each section is exposed to substantially similar environmental conditions. In one embodiment, a first section of the reference arm and a first section of the sample arm are at least partially disposed in the dock. In one embodiment, the dock is configured to receive and hold the patient interface unit. In one embodiment, the dock is configured to receive wireless data from the data collection probe, and further includes a user interface device that includes a touch screen, a selecting unit configured to select between the data collection probe and a pressure transducer-based device, and a graphical user interface, the user interface device configured to display images generated using image data or a pressure data-based parameter and to receive user inputs. In one embodiment, the patient interface unit is configured to receive an intravascular ultrasound imaging probe. In one embodiment, the data collection probe is configured to collect the optical coherence tomography data and one or both of ultrasound data and pressure data.

In one embodiment, the system further includes a first converter configured to receive electrical ultrasound signals generated using the data collection probe and convert the electrical ultrasound signals into optical signals for transmission to a second converter. In one embodiment, the system further includes a first converter configured to receive electrical pressure signals generated using the data collection probe and convert the electrical pressure signals into optical signals for transmission to a second converter. In one embodiment, the system further includes a third optical fiber disposed in the protective sheath, the third optical fiber configured to transmit pressure data or ultra sound data received from the data collection probe. In one embodiment, the system further includes a digital communication fiber or an electrical wire disposed in the protective sheath.

In one aspect, the invention relates to an image data collection system. The system includes an interferometer includes a reference arm that includes a first optical fiber of length of L1 and a sample arm that includes a second optical fiber of length of L2; and a first rotary coupler configured to interface with an optical tomography imaging probe, wherein the rotary coupler is in optical communication with the sample arm and wherein L2 is greater than about 5 meters.

In one embodiment, the first optical fiber and the second optical fiber are both disposed in a common protective sheath. In one embodiment, the system further includes an optical element configured to adjust the optical path length of the reference arm, wherein the optical element is in optical communication with the reference arm and wherein the optical element is transmissive or reflective. In one embodiment, the lengths L1 and L2 and the disposition of the first optical fiber and the second optical fiber in the common protective sheath are configured to substantially reduce degradation of an image formed using data collected by the optical tomography imaging probe. In one embodiment, the system further includes an electrically conductive wire disposed within the protective sheath. In one embodiment, the system further includes an ultrasound system that includes an electrical to optical converter configured to receive an electrical signal that includes ultrasound data and convert the electrical signal to an optical signal. In one embodiment, the ultrasound system includes a third optical fiber of length of L3, wherein the third optical fiber is configured to conduct the optical signal between a first location in which the first interferometer is positioned and a second location in which the rotary coupler is positioned, the third optical fiber having a first end and a second end. In one embodiment, the first interferometer is installed in a first room and the rotary coupler is disposed in a second room and the length of the protective sheath is sized to optically couple the first rotary coupler and the sample arm via the second optical fiber.

In one embodiment, the system further includes a server configured to collect image data and a portable wireless control station that includes a display, and one or more input devices, wherein the portable control station is configured to control at least one of the server and image data collection by the optical tomography imaging probe. In one embodiment, the system further includes a circulator and a reflective or transmissive variable path length mirror in optical communication with the reference arm and the circulator. In one embodiment, the system further includes a fiber Bragg grating and a photodetector, wherein the reference arm is in optical communication with the fiber Bragg grating and the photodetector. In one embodiment, the photodetector is configured to transmit a pulse for synchronizing ultrasound data collection and OCT data collection in response to a received wavelength from the fiber Bragg grating. In one embodiment, the common protective sheath has a length greater than about 5 meters. In one embodiment, the server includes a data acquisition device with two channels, wherein one channel is configured to acquire data according to a variable frequency external clock.

In one embodiment, the system further includes one or more switches; a server; and one or more interface systems, each interface system in communication with a respective switch, each interface system configured to interface with the optical coherence tomography probe, a pressure wire or an ultrasound probe, wherein the server is configured to collect data from each interface system. In one embodiment, the system further includes an optical coupler having a first, second and third arm, the first arm of the optical coupler in optical communication with the one or more switches; a mirror in optical communication with the second arm of the optical coupler; and a circulator having a first, second and third port, the first port being in optical communication with the optical coupler, the second port in optical communication with a fiber Bragg grating, and a third port in optical communication with a photodetector, wherein the photodetector generates a trigger signal when a certain wavelength occurs in the optical signal from the one or more switches.

In one embodiment, the system further includes a user interface device that includes a touch screen, a selecting unit configured to select between the optical tomography imaging probe and a pressure transducer-based device, and a graphical user interface, the user interface device configured to display images generated using image data or a pressure data-based parameter and to receive user inputs. In one embodiment, the user interface device is component of a mobile terminal in electrical or optical communication with a server configured to receive data from the optical tomography imaging probe. In one embodiment, each interface system includes an interface dock and an interface unit, wherein the interface dock provides an optical-electrical interface between the interface unit and the server. In one embodiment, the system further includes a variable path length air gap in optical communication with the reference arm. In one embodiment, the system further includes a first wavelength division multiplexing filter in optical communication with the first end of the third optical fiber and a second wavelength division multiplexing filter in optical communication with the second end of the third optical fiber. In one embodiment, the first optical fiber, the second optical fiber, and the third optical fiber and a strength member are all disposed in a common protective sheath.

In one aspect, the invention relates to an intravascular data collection system. The system includes a computer that includes a digitizer having one or more inputs to receive at least one of an optical coherence tomography probe generated signal or an ultrasound transducer generated signal; an imaging engine that includes a light source; a patient interface unit that includes a rotary coupler; a first wireless pressure data receiver configured to receive pressure wire data; a patient interface dock that includes a reference optical element; and an interferometer that includes a reference arm that includes a first optical fiber of length of L1 and a sample arm that includes a second optical fiber of length of L2, wherein the rotary coupler is in optical communication with the sample arm, wherein the reference optical element is in optical communication with the reference arm, wherein the light source is in optical communication with the sample arm. In one embodiment, the first optical fiber and the second optical fiber are both disposed in a common protective sheath. In one embodiment, L2 is greater than about 5 meters. In one embodiment, the system further includes an optical element configured to adjust the optical path length of the reference arm, wherein the optical element is in optical communication with the reference arm and wherein the optical element is transmissive or reflective.

In one embodiment, the system further includes a variable path length air gap in optical communication with the reference arm. In one embodiment, the system further includes a user interface device that includes a touch screen, a selecting unit configured to select image data collected using the sample arm, and a graphical user interface, the user interface device configured to display images generated using image data, one or more FFR values generated using pressure wire data and to receive user inputs. In one embodiment, the system further includes a second wireless pressure data receiver configured to receive aortic pressure data. In one embodiment, the system further includes a matching unit configured to match an interface unit with a stored interface unit identity, wherein the interface unit is configured to wirelessly relay pressure wire data to the first pressure data receiver. In one embodiment, the system further includes a selection unit configured to select between one or more OCT procedure rooms or one or more interface units based on a received control signal or selection rule.

In one aspect, the invention relates to a method for co-registering angiographic image data with intravascular optical tomography data. The method includes providing an angiography system proximal to a support configured to position a patient in a catheterization laboratory; providing an intravascular optical tomography system that includes an imaging engine that includes an optical radiation source; an interferometer that includes a reference arm that includes a first optical fiber of length of L1 and a sample arm that includes a second optical fiber of length of L2; a patient interface unit configured to interface with an optical tomography imaging probe, wherein the patient interface unit is in optical communication with the sample arm; a computer configured to receive and process image data from the optical tomography imaging probe and generate images; and a monitor for displaying the images, wherein the imaging engine and the computer are located remotely from the support and the patient interface unit and monitor are located proximal to the support; simultaneously collecting angiography data and intravascular optical tomography data with respect to a vessel disposed in the patient; and co-registering the angiography data and intravascular optical tomography data.

In one embodiment, the method further includes transmitting angiography data from the angiography system to the intravascular optical tomography system. In one embodiment, the method further includes transmitting intravascular optical tomography data from the intravascular optical tomography system to the angiography system. In one embodiment, the intravascular optical tomography data and angiography data are communicated to a third system for co-registration.

In one aspect, the invention relates to an image data collection system for acquiring a first set of images of a first patient disposed on a first support in a first examination room and a second set of images of a second patient disposed on a second support in a second examination room. The system includes an imaging engine that includes an optical radiation source; a first reference arm that includes a first optical fiber of length of L1; a first sample arm that includes a second optical fiber of length of L2; a second reference arm that includes a third optical fiber of length of L3; a second sample arm that includes a fourth optical fiber of length of L4; an optical switch directing optical radiation from the imaging engine to one of the first reference and first sample arms or second reference and second sample arms; wherein the first reference arm and the first sample arm are in optical communication with the imaging engine and a first patient interface unit in the first examination room; wherein the second reference arm and the second sample arm are in optical communication with the imaging engine and a second patient interface unit in the second examination room; a computer configured to receive and process image data from the first and second sample arms and generate a first set of image and a second set of images; a first monitor for displaying the first set of images in the first examination room; a second monitor for displaying the second set of images in the second examination room; and wherein the imaging engine and the computer are located remotely from the first support and the second support, the first patient interface unit and first monitor are located proximal to the first support and the second patient interface unit and second monitor are located proximal to the support.

In one aspect, the invention relates to an image data collection system. The system includes a patient interface system that includes a section of a sample arm of an interferometer defining a first optical path, wherein one end of the first optical path is configured to receive optical coherence data received from a data collection probe; a first converter configured to receive electrical ultrasound data and convert the electrical ultrasound data to an optical signal; and an optical device defining a second optical path, the optical device in optical communication with the first converter and configured to transmit the optical signal to a second converter.

In one embodiment, the system further includes a patient interface unit dock that includes a housing, wherein the section of the sample arm of the interferometer, the first converter, and the optical device are at least partially disposed within the housing; and a patient interface unit that includes a coupler in optical communication with and disposed between the section of the sample arm of the interferometer and the data collection probe, a drive motor configured to rotate an optical fiber disposed in the data collection probe, and a receiver configured to receive ultrasound data generated using the data collection probe or an intravascular ultrasound probe. In one embodiment, the system further includes an imaging engine that includes a light source; the interferometer in optical communication with the light source; and the second converter. In one embodiment, the system further includes a server that includes a data acquisition device in electrical communication with the second converter.

In one aspect, the invention relates to a method of generating an optical coherence tomography image of a portion of a subject disposed on a support. The method includes transmitting light from a light source at a first location along a sample arm of an interferometer and a reference arm of the interferometer, the sample arm terminating at a second location and the reference arm terminating at a third location, wherein the distance between the first location and second location is greater than about 5 meters, the second location disposed within the subject and near the portion of the subject; receiving light scattered from the portion of the subject at a data collection probe in optical communication with the sample arm; receiving light scattered from a reflector in optical communication with the sample arm; combining the light received from the data collection probe and the light scattered from the reflector to generate interference data; and generating the optical coherence tomography image in response to the interference data.

In one embodiment, the third location is in a patient interface dock. The method can further include collecting ultrasound data with respect to the portion, the ultrasound data that includes a first electrical signal. The method can further include converting the first electrical signal to an optical signal and transmitting the optical signal along an optical fiber to a fourth location. The method can further include converting the optical signal to a second electrical signal. The method can further include generating a second image of the portion of the subject using the second electrical signal. The method can further include co-registering the optical coherence tomography image and the second image.

In one aspect, the invention relates to a multimodal imaging system including an imaging engine having a plurality of switches; a server in communication with the imaging engine; and a plurality of interface systems, each interface system in communication with respective ones of the plurality of switches; each interface system constructed to also interface with an OCT and ultrasound probe, and wherein the server controls the taking and processing of images from the OCT probes and the ultrasound probes interfaced with the plurality of interface systems.

In one aspect, the invention relates to an image data collection apparatus. The apparatus includes a plurality of switches; a server; and a plurality of interface systems, each interface system in communication with a respective one of the plurality of switches, each interface system configured to interface in with at least one optical coherence tomography probe or ultrasound probe, wherein the server is configured to collect data from each interface system.

In one embodiment, each switch of the plurality of switches is an optical switch. Each of the plurality of interface systems can be connected to the switch by a respective optical cable. Each respective optical cable of the plurality of optical cables can be of a length sufficient to permit each of the plurality of interface systems to be located in a different room. The server can be in electronic communication with an angiography system.

The server can be configured and/or programmed to display co-registered optical coherence tomography, ultrasound and angiographic images. The imaging engine can include a Mach-Zehnder interferometer (MZI). The MZI can be configured to generate a clock signal. The apparatus can include a delay device in communication with the Mach-Zehnder interferometer. The delay device can be configured to delay the clock signal to assure alignment between the clock signals and digitized interference signals. The delay device can be an electronic delay device or an optical delay device. In one embodiment, intervals between the rising or falling edges of sequential clock signals are varied according to a user-selected delay to compensate for residual dispersion in the optical coherence tomography signals.

Each interface system can include an interface dock and an interface unit. An interface dock can include or provide an optical-electrical interface between the interface unit, the server and the imaging engine. As part of this interface a converter can be included. The converter can be used to transform ultrasound data from an electrical signal to an optical signal. The interface dock can include a reflective mirror in optical communication with the reference arm of a Michelson interferometer. The interface dock can include a trigger device. The trigger device can include an optical coupler having a first, second and third arm, the first arm of the optical coupler in optical communication with one of the plurality of switches; a mirror in optical communication with the second arm of the optical coupler; and a circulator. In one embodiment, the circulator has a first, second and third port, the first port being in optical communication with the optical coupler, the second port in optical communication with a fiber Bragg grating, and a third port in optical communication with a photodetector. The photodetector can be configured to generate a trigger signal when a certain wavelength occurs in the optical signal from the one of the plurality of switches. In one embodiment, the trigger signal initiates the generation of an ultrasound pulse synchronously with illumination by a sample light from a sample arm of an interferometer.

The server can include a data acquisition device or component, such as a digitizer, with two channels wherein at least one channel is configured to acquire data according to a variable frequency external clock; wherein one channel is configured to acquire optical coherence tomography data; and wherein a second channel is configured to acquire ultrasound data. In one embodiment, the optical coherence tomography channel is sampled in response to a time-varying external clock signal. In one embodiment, the ultrasound channel is sampled in response to fixed clock signal. In one embodiment, the ultrasound channel is acquired at a line rate that differs from the line rate of the optical coherence tomography channel by a factor that ranges from about 1 to about 0.0625.

The apparatus can include a first optical coupler; a first optical circulator having a first port in optical communication with the optical coupler, a second port in communication with a variable path length mirror, a third port in optical communication with a first switch of the plurality of switches, and a fourth port in optical communication with a polarization controller; a second optical circulator having a first port in optical communication with the first optical coupler, a second port in optical communication with a mirror, a third port in optical communication with a second switch of the plurality of switches, and having a fourth port; a balanced detector having a first input port and a second input port and having an output terminal; and a second optical coupler, having a first port in optical communication with the polarization controller, a second port in optical communication with the fourth port of the second circulator, a third port in optical communication with first input port of the balanced detector and a fourth port in optical communication with the second input port of the balanced detector.

The apparatus can include a first optical coupler; a first optical circulator having a first port in optical communication with the optical coupler, a second port in communication with a variable path length mirror, a third port in optical communication with a first switch of the plurality of switches, and a fourth port in optical communication with a polarization controller; a second optical circulator having a first port in optical communication with the first optical coupler, a second port in optical communication with a mirror, a third port in optical communication with a second switch of the plurality of switches, and having a fourth port; a first balanced detector having a first input port and a second input port and having an output terminal; a second balanced detector having a first input port and a second input port and having an output terminal and a second optical coupler; a third optical coupler; a fourth optical coupler; a fifth optical coupler; and a sixth optical coupler; the second optical coupler in optical communication with the polarization controller, the third optical coupler, and the fifth optical coupler, the fifth optical coupler in optical communication with the sixth optical coupler, the sixth optical coupler in optical communication with the second balanced detector, the third optical coupler in optical communication with the first balanced detector, the fourth optical coupler in optical communication with the third optical coupler and the fourth port of the second optical circulator.

The apparatus can include a first optical coupler; a first optical circulator having a first port in optical communication with the optical coupler, a second port in communication with a variable path length air gap (VPLAG), the VPLAG in optical communication with a first switch of the plurality of switches, and a third port in optical communication with a polarization controller; a second optical circulator having a first port in optical communication with the first optical coupler, a second port in optical communication with a second switch of the plurality of switches, and having a third port; a balanced detector having a first input port and a second input port and having an output terminal; and a second optical coupler, having a first port in optical communication with the polarization controller, a second port in optical communication with the third port of the second circulator, a third port in optical communication with first input port of the balanced detector and a fourth port in optical communication with the second input port of the balanced detector.

The apparatus can include a first optical coupler; a first optical circulator having a first port in optical communication with the optical coupler, a second port in communication with a variable path length mirror, a third port in optical communication with a first switch of the plurality of switches, and a fourth port in optical communication with a polarization controller; a second optical circulator having a first port in optical communication with the first optical coupler, a second port in optical communication with a mirror, a third port in optical communication with a second switch of the plurality of switches, and having a fourth port; a balanced detector having a first input port and a second input port and having an output terminal; and a second optical coupler, having a first port in optical communication with the polarization controller, a second port in optical communication with the fourth port of the second circulator, a third port in optical communication with first input port of the balanced detector and a fourth port in optical communication with the second input port of the balanced detector.

In one aspect, the invention relates to a data collection system that includes an optical coherence tomography system that can include a first interferometer that can include a reference arm that can include a first optical fiber of length of L1, and a sample arm that includes a second optical fiber of length of L2, wherein the first optical fiber and the second optical fiber are both disposed in a common cable and a first rotary coupler configured to interface with an optical tomography imaging probe, wherein the rotary coupler is in optical communication with the sample arm. The first interferometer can be installed in a first room and the rotary coupler is disposed in a second room and the cable is sized to optically couple the first rotary coupler and the sample arm via the second optical fiber of length L2. The first optical fiber of length L1 can be in optical communication with a reflective mirror. Additional interferometers can be used at the same or different locations relative to the first interferometer.

The optical coherence tomography system further can include an optical switch having a first port in optical communication with the sample arm and a second port in optical communication with the first rotary coupler. The optical coherence tomography system further can include a circulator and a reflective or transmissive variable path length mirror in optical communication with the reference arm and the circulator. The optical coherence tomography system further can include a fiber Bragg grating and a photodetector, wherein the reference arm is in optical communication with the fiber Bragg grating and the photodetector. In one embodiment, the photodetector is configured to transmit a pulse for synchronizing ultrasound data collection and OCT data collection in response to a received wavelength from the fiber Bragg grating.

The data collection system can further include an ultrasound system that includes an electrical to optical converter configured to receive an electrical signal that includes ultrasound data and convert the electrical signal to an optical signal. The ultrasound system can include an optical switch and a third optical fiber of length of L3, wherein the third optical fiber conducts the optical signal between a first room in which the interferometer is disposed and a second room in which the rotary coupler is disposed. The data collection system can further include a digitizer having a first channel and a second channel, wherein the first channel receives a signal from the optical coherence tomography system and the second channel receives a signal from the ultrasound system.

In one embodiment, the optical coherence tomography data is digitized according to a variable frequency clock and the ultrasound signal is digitized according to a fixed frequency clock. The dock can include a mirror in optical communication with a first switch of the plurality of switches and a first WDM filter in optical communication with both a second switch of the plurality of switches and a second WDM filter, wherein the second WDM filter is in optical communication with the second switch of the plurality of switches. The data collection system can be configured such that L1 and L2 are greater than about 5 meters. The fibers associated with L1 and L2 can be in the same or locations. The interface dock can include at least one wireless receiver for receiving intravascular pressure data.

In one aspect, the invention relates to an intravascular data collection system that includes a first primary data collection element that includes a digitizer having one or more inputs to receive at least one of an OCT related signal, a FFR related signal, and an ultrasound related signal; a first supplemental data collection element that includes a probe that includes an optical fiber; a second supplemental data collection element that includes a subset of a sample arm; a network having a first topology with a central node, a first auxiliary node and a second auxiliary node connected by a first link and a second link respectively, wherein the first primary data collection element is positioned at the central node and the first and second supplemental data collection elements are disposed at the respective first and second auxiliary nodes, wherein the auxiliary nodes are disposed a distance D1 and D2 from the central node. Each link can include an optical fiber and an electrical conductor disposed in a common enclosure. At least one link can include a portion of an arm of an interferometer. At least one link can include a reference arm that includes a first optical fiber of length of L1, and a sample arm that includes a second optical fiber of length of L2, wherein the first optical fiber and the second optical fiber are both disposed in protective sheath such as for example a common cable or jacket or other covering.

In part, the invention relates to systems, methods and devices, such as input devices, controllers and interfaces that improve the process of initiating a measuring procedure, such as an OCT, IVUS, or pressure-wire based procedure and to provide procedures for configuring and installing a monitoring device that reduce error and setup time.

In part, the invention relates to systems, methods and devices, such as input devices, controllers and interfaces that improve flexibility of the measurement equipment such that different desired measurement units quickly and easily can be connected and disconnected. Thus, a plug and play configuration for an OCT system, a pressure wire system, other imaging and pressure measuring modalities, and combinations thereof are embodiments of the invention.

In part, the invention relates to systems, methods and devices that support graphical interfaces and displays, such as display screen-based or touch screen based interfaces, and the displays themselves that improve and facilitate user interaction with a monitoring device or facilitate mobile use or use from a remote location relative to a room, a catheter lab, or other location.

In one embodiment, the invention relates to a probe, which can include a pressure or imaging probe, for monitoring, analysing, and displaying physiological conditions related to pressure in a vessel such as blood pressure. The device can include a pressure wire receiver unit configured to receive a wireless signal representing a measured physiological, or other, variable in the living body, an aortic blood pressure receiver unit configured to receive, from at least one aortic pressure interface unit, a wireless signal including interface identity information required to identify the interface unit, and information representing measured aortic blood pressure, a signal processing element or subsystem configured to calculate blood pressure related parameters, a touch screen configured to display information regarding selectable aortic pressure interface units and blood pressure related parameters, and to receive user input, an identifying unit configured to identify interface units based upon received interface identity information, a presentation unit configured to present, on the touch screen, the interface unit(s) identified by the identifying unit, a selecting unit configured to select one of the presented interface units, and wherein the aortic blood pressure receiver unit is configured to receive aortic pressure information from the selected aortic pressure interface unit.

According to another aspect, the invention also relates to an optical coherence tomography system that includes a probe, which can include a pressure or imaging probe, wherein the system includes a display configured to provide a graphical interface to a system operator or use. According to a further aspect, the invention relates to method for setting up a probe.

In part, the invention relates to installing, configuring or otherwise setting up a probe, which can include a pressure or imaging probe, for monitoring, analysing, and displaying physiological conditions related to blood pressure. The method includes receiving, from at least one aortic pressure interface unit, a wireless signal including interface identity information required to identify the interface unit; displaying on a touch screen information regarding selectable aortic pressure interface units; identifying interface units based upon received interface identity information; presenting the identified interface unit(s) on the touch screen; selecting one of the presented interface units; and receiving aortic pressure information from the selected aortic pressure interface unit.

In one embodiment, the method includes matching identified interface units with a set of stored interface unit identities, and presenting, on the touch screen, the interface unit(s) having a positive match. In one embodiment, the method includes selecting one of the presented interface units in response of a user input on the touch screen. In one embodiment the method includes selecting one of the presented interface units automatically according to predetermined selecting rules. In one embodiment, the method the predetermined selecting rules includes parameters related to the received wireless signal. In one embodiment the method includes receiving calibration data related to the selected aortic pressure interface unit.

In one embodiment, the invention relates to a patient data collection system for monitoring, analysing, and displaying physiological conditions. The system includes a pressure wire receiver unit configured to receive a wireless signal representing a measured physiological, or other, variable in the living body; an aortic blood pressure receiver unit configured to receive, from at least one aortic pressure interface unit, a wireless signal including interface identity information required to identify the interface unit, and information representing measured aortic blood pressure; a signal processing means configured to calculate blood pressure related parameters; a touch screen configured to display information regarding selectable aortic pressure interface units and blood pressure related parameters, and to receive user input; an identifying unit configured to identify interface units based upon received interface identity information; a presentation unit configured to present, on the touch screen, the interface unit(s) identified by the identifying unit; and a selecting unit configured to select one of the presented interface units, and wherein the aortic blood pressure receiver unit is configured to receive aortic pressure information from the selected aortic pressure interface unit. The system further includes a matching unit that is configured to match identified interface units with a set of stored interface unit identities, and wherein the presentation unit is configured to present, on the touch screen, the interface unit(s) having a positive match. The selection by the selecting unit can be made in response of a user input on the touch screen. The selection by the selecting unit can be made automatically according to predetermined selecting rules. The predetermined selecting rules include parameters related to the received wireless signal. The aortic blood pressure receiver unit can be configured to receive calibration data related to the selected aortic pressure interface unit. The pressure wire receiver unit and/or the aortic blood pressure receiver unit can be detachable. The pressure wire receiver unit is connectable to the device via a USB connection. The aortic blood pressure receiver unit is connectable to the device via a USB connection.

In one embodiment, the invention relates to a system for monitoring, analysing, and displaying physiological conditions related to blood pressure within a living body. The system includes at least one aortic pressure interface unit configured to receive information representing measured aortic blood pressure, and to transmit a wireless signal including interface identity information required to identify the interface unit, and information representing the measured aortic blood pressure.

In one embodiment, the invention relates to a method of setting up a probe, which can include a pressure or imaging probe, for monitoring, analysing, and displaying physiological conditions. The method includes receiving, from at least one aortic pressure interface unit, a wireless signal including interface identity information required to identify the interface unit; displaying on a touch screen information regarding selectable aortic pressure interface units; identifying interface units based upon received interface identity information; presenting the identified interface unit(s) on the touch screen; selecting one of the presented interface units; receiving aortic pressure information from the selected aortic pressure interface unit. The method can further include matching identified interface units with a set of stored interface unit identities, and presenting, on the touch screen, the interface unit(s) having a positive match. The method can further include selecting one of the presented interface units in response of a user input on the touch screen. The method can further include selecting one of the presented interface units automatically according to predetermined selecting rules. The method can further include predetermined selecting rules includes parameters related to the received wireless signal. The method can further include receiving calibration data related to the selected aortic pressure interface unit.

This Summary is provided merely to introduce certain concepts and not to identify any key or essential features of the claimed subject matter.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

FIG. 2A depicts an interferometer that incorporates a long sample arm and long reference arm together with a reflective variable path length mirror and other components in accordance with an illustrative embodiment of the invention.

FIGS. 8A-8C depict cross-sections of embodiments of cables used to connect a PIU dock to an imaging engine and data acquisition computer in accordance with an illustrative embodiment of the invention.

DETAILED DESCRIPTION

Figure 1A:
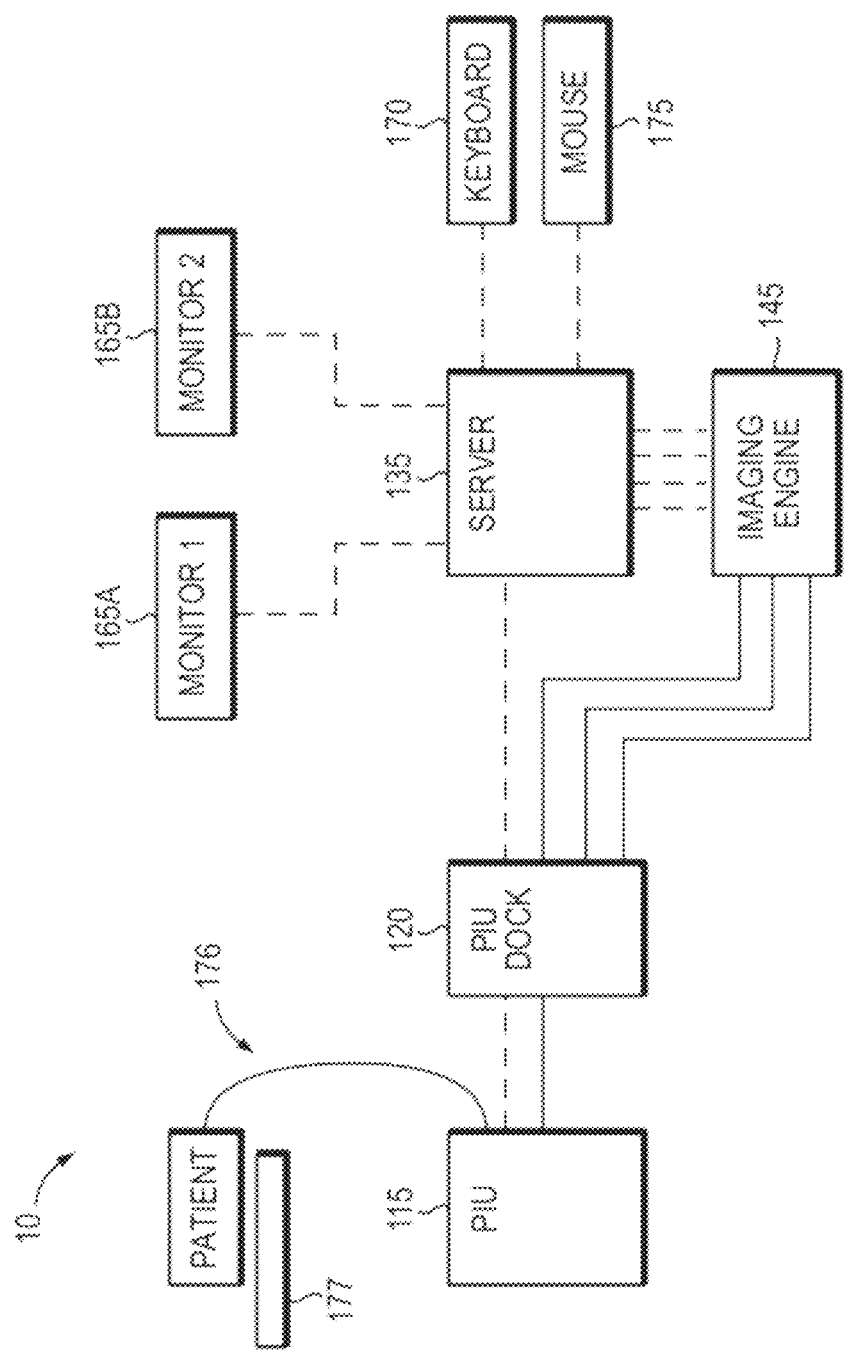
FIG. 1A depicts a block diagram of an embodiment of a multimodal data collection system in accordance with an illustrative embodiment of the invention.

As described above, there are limitations to currently known intravascular diagnostic systems. In part, the invention relates to various systems and components thereof for use in a catheter lab or other facility to collect data from a patient and help improve upon one or more of these limitations. The data collected is typically related to the patient's cardiovascular or peripheral vascular system and can include image data, pressure and other types of data as described herein. In addition, in one embodiment image data is collected using optical coherence tomography (OCT) probes and other related OCT components. OCT is an imaging modality that uses interferometry to determine distances and other related measurements. As such, one or more embodiments of the invention relate to interferometer designs that are configured for longer sample and/or reference arms while maintaining image data levels within desirable quality levels or otherwise compensating for certain unwanted noise or other environmental effects.

In addition, some embodiments of the invention are suitable for handling multiple imaging modalities. Thus, in part, the invention relates to a multimodal diagnostic system and components thereof incorporating one or more of the following data collection modalities into a single system or apparatus OCT, IVUS, FFR, and angiography. OCT system improvements are described that enable location of the patient interface unit (PIU) and imaging probe remotely from the imaging engine and/or server. This can be accomplished over distances of between about 5 to about 100 meters (and greater in some embodiments). Using one or more interferometers with a longer reference sample and/or reference arm can facilitate this separation of the imaging probe from one or more OCT system components. The inclusion of switches such as optical switches or electronic switches to route control and/or image data signals can also be advantageous as described herein.

IVUS imaging capabilities can also be incorporated into a system embodiment using the same or an additional PIU. FFR pressure measurements can also be performed using FFR probes. For example, FFR probes having wireless transmitters can be used. Specifically, such an FFR probe can send FFR data to one or more wireless receivers which can in turn transmit FFR data to the server. Comparison and co-registration of OCT and/or IVUS images with angiographic images can be achieved using different configurations. For example, the data collection system (OCT, IVUS, FFR, etc.) can be configured to interface with an angiography device (or vice versa). Alternatively, the data collection system can be configured to interface with a hospital data network wherein the angiographic data is stored. In one embodiment, the PIU includes various elements such as an electro-optic rotary coupler, rotational motor, linear travel stage, ultrasound controller, and motion controller.

To reduce clutter in the procedure room where a pullback is performed, in one embodiment, a single system or apparatus is used to dock the PIU as well as to route optical and electrical signals between the PIU, control panel, imaging engine, and data acquisition apparatus. This system apparatus is a PIU dock in one embodiment. The PIU connects to the PIU dock by mechanical fit. Docking may be assisted through the use of magnets or interlocking mechanical features on the PIU and PIU dock. An electrical connector and an optical connector are also used to place the PIU in electrical and/or optical communication with the PIU dock. To reduce capital costs, a single imaging engine and data acquisition system capable of supporting diagnostic equipment in multiple procedure rooms can also be used.

Referring to FIG. 1A, one embodiment of a multimodal diagnostic system or data collection system 10 may include: an imaging engine 145; a server or computer 135 (referred to hereafter as a server) containing a data acquisition device such as a digitizer; a PIU dock 120; a PIU 115; input/output devices such as monitors 165a and 165b, a keyboard 170 and a mouse 175. To permit near-simultaneous control by more than one operator, more than one keyboard or mouse can be employed. The imaging engine may include one or more of a tunable laser, fiber-optic interferometers, polarization controllers, opto-electrical converters, electro-optical converters, optical switches, electrical receivers and signal conditioners, and/or control systems for controlling these components. The PIU is in optical communication with a data collection probe along an optical path 176 that can be defined by an optical fiber in one embodiment. When configured as an integrated system, the imaging engine 145 and server 135 may be located in a separate control room. The PIU dock 120, PIU 115, and input/output or control devices 165a and 165b, 170 and 175, respectively, may be located remotely in a procedure room, adjacent to a patient examination table or another common patient reference such as a support 177. A support can include a bed, an operating table, or other apparatuses suitable for positioning a patient during a data collection procedure. In one embodiment, the PIU dock 120 includes a housing configured to receive and/or store the PIU 115 when the PIU 115 is not being used with a probe as part of a data collection procedure. In FIG. 1A major optical connections are shown as solid lines, while electrical connections are shown as dashed lines. In one embodiment, an electrical connection can include a wireless or wired connection. The keyboard 170 and mouse 175 can be used as part of a mobile terminal that can move between rooms as described below.

As shown in FIG. 1A, the system 10 has various features relating to the ability to position the various components relative to the patient during a procedure. Given that the patient is disposed on a support 176 during a data collection procedure, the support 177 can serve as a frame of reference. The PIU 115 is in optical communication with the data collection probe inserted in the patient and thus is in the vicinity of or proximal to the patient and thus the support 176. The probe is used to collect data with respect to a portion of a vessel of the patient in one embodiment. In addition, the probe includes an optical fiber that terminates in the patient and thus, in one embodiment, is the terminus of the sample arm. The PIU Dock 120 can also be in the vicinity of or proximal to the patient or the support such that a procedure, such as a data collection session by which a blood vessel of the patient is imaged, can be performed.

A display, which can be one of the monitors 165a, 165b, or other display, can also be in the vicinity of or proximal to the patient or support 177. The display can be configured to display the image generated in response to the interference data collected with the probe. In one embodiment, the PIU dock can be remote from the patient or support 177 such that the clinician or other system user has access to the PIU in the vicinity of the patient. The PIU can be attached to the support 177 in one embodiment. The server 135, imaging engine 145, one or both monitors 165a, 165b, and the keyboard 170 and mouse 175 can also be remote from the patient or support 177. The data collected with respect to the patient can include OCT data, IVUS data, pressure data, and other data relevant to the patient's health and/or the characteristics of the blood vessel being imaged. Unlike an IVUS only system, which is not an optical imaging modality, allowing remote optical elements alone and in combination with IVUS imaging modalities and pressure measuring devices to operate remotely from the support 177 requires various optical components and systems designed for this purpose. Given the complexities of interferometry, optical signal transmission and noise reduction, various embodiments of the invention relate to addressing the challenges of remotely locating or allowing flexibility of moving some of the optical components of a data collection system between rooms or between different locations. In addition, the challenge of integrating different signals, such as acoustic, electrical, and optical signals are also addressed with different embodiments as described herein.

The system 10 can be used with a patient as shown with the various elements of the system being located in the vicinity of the patient or proximal to the patient. Alternatively, certain components of the system 10 can be positioned remotely from the patient such as in other parts of the same procedure room the patient is in, but not near the patient for use by an operator or clinician or in a different room relative to the patient. This can be facilitated by the patient being disposed in a support 177 during a probe-based data collection procedure. An optical fiber portion connects the PIU 115 to the patient as shown. The PIU dock 120 and the PIU 115 are typically near a patient such as connected to or positioned near the support 177.

Figure 1B:
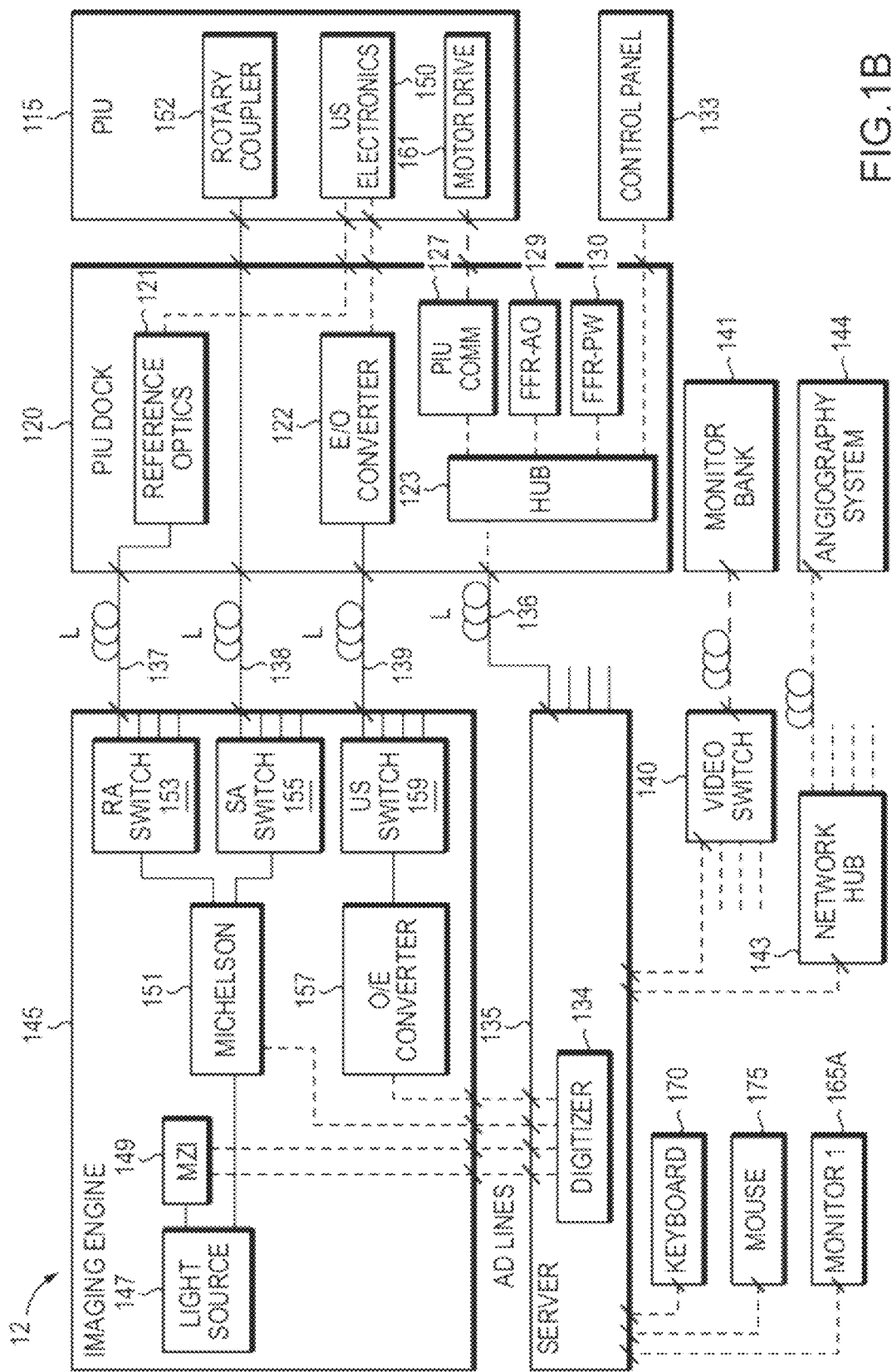
FIG. 1B depicts a more detailed block diagram of an embodiment of a multimodal data collection system in accordance with an illustrative embodiment of the invention.

Referring also to FIG. 1B, the system 12, in more detail, includes in one embodiment, an imaging engine 145 that includes a light source 147, a Mach-Zehnder Interferometer (MZI) 149, and a Michelson interferometer 151 or one or more other OCT system components. The system 12 of FIG. 1B is configured to allow the same remote and proximal positioning of different system components as otherwise described herein with different embodiments. As shown, two signal lines are in communication with the MZI 149 from the digitizer 134 of the server 135. One of these signal lines is a line trigger, such as for example the line connected to the Bragg grating 370 of FIG. 3 and, the other signal line is the k clock, which can be the k clock signal in FIG. 3. The line trigger and the k clock can be sent to the MZI from the digitizer 134. The light source 147 may be any device that produces a swept wavelength output as a function of time. The light source can be selected for use in frequency-domain, swept-source, or Fourier-domain OCT (generically FD-OCT). The system 12 may also be configured as a spectral domain (SD-OCT) or time domain (TD-OCT) OCT system by incorporating a suitable light source 147 such as a broadband light source and spectrometer, in the case of SD-OCT.

In one embodiment, the imaging engine 145 can also include a reference arm (RA) optical switch 153, a sample arm (SA) switch 155, and an ultrasound (US) switch 159 in communication with an opto-electrical (O/E) converter 157. As used herein, US refers to ultrasound such as an IVUS or other ultrasound-based data collection modality. In one embodiment, US can also include pressure transducer data such as data suitable for FFR measurements. However, in one embodiment the imaging engine may only include a digitizer and/or a light source such as a laser. The switches can be controlled by control lines in the imaging engine 145. Electrical signals from the MZI 149, the Michelson interferometer 151 and the O/E converter 157, are sent to a digitizer 134 within the server 135. The positions of the ultrasound switch 159 and O/E converter 157 may also be reversed, such that the US switch 159 is an electrical switch instead of an optical switch and the O/E converter 157 is a multi-channel O/E converter.

Control signals from the server 135 are sent to the PIU dock 120 by way of an optical link 136. Input/output devices such as a keyboard 170, mouse 175 and monitor 165a provide an interface to the server 135 for an operator. The server 135 in various embodiments is connected to a hospital network through a network hub 143 and receives angiography data from an angiography system 144 through the network hub 143. A video switch 140 provides video information to one or more video monitors 141 in various locations as applicable.

The PIU dock 120 is connected by optical cable 137 to the RA switch 153. Light is communicated to and from the RA switch 153 from and to, respectively, the reference optics 121 of the PIU dock 120. The converted optical signals are sent to and used by the ultrasound electronics 150 of the PIU 115. Similarly, light is communicated to and from the SA switch 155 by an optical cable 138 from and to, respectively, a rotary coupler 152 of the PIU 115. The PIU 115 is in optical communication with a length of optical fiber that is part of the sample arm as shown. This length of fiber is connected to a data collection probe disposed in a subject such as a patient prior to collecting image data or other data. Finally optical signals pass to the US switch 159 of the imagining engine 145 over an optical cable 139 from an electrical to optical (E/O) converter 122 of the PIU dock 120. In one embodiment, electrical signals from the ultrasound electronics 150 of the PIU 115 are sent to the E/O converter 122.

Signals from the server 135 communicated to the PIU dock 120 over the optical cable 136 enter the hub 123. Electro-optical conversion takes place in the server 135, while opto-electrical conversion takes place in a converter in the hub 123. Other conversion devices and configurations relating to when and what devices perform conversion can be used. The hub 123 sends and receives instructions to and from a control panel 133 and to and from a PIU communications port 127 which is used to control motion of the motors of the PIU 115. The motors of the PIU can be used to rotate and pullback an OCT and/or ultrasound imaging probe interfaced therewith or other functions. The hub 123 also provides control signals and receives measurement data to and from the FFR-AO 129 and FFR-PW 130 receivers as described below. AO refers to aortic pressure and PW refers to pressure wire in one embodiment. The pressure data receivers 129, 130 can be used to receive pressure data from one or more pressure transducers and can be used for FFR measurements and other purposes. In one embodiment, pressure data is wirelessly transmitted to the pressure data receivers.

Figure 1C:
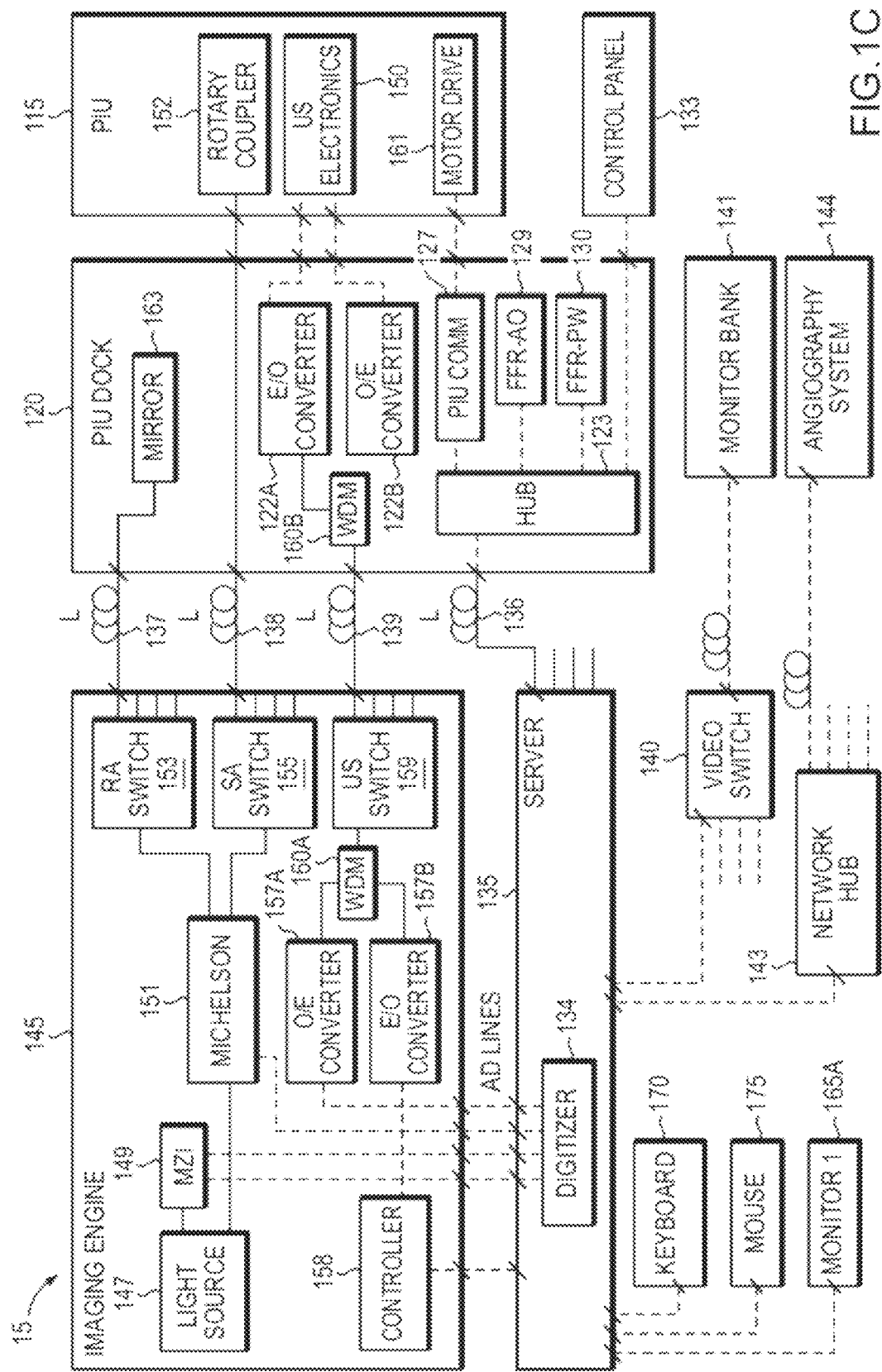
FIG. 1C depicts an alternate embodiment of a multimodal data collection system in accordance with an illustrative embodiment of the invention.

FIG. 1C shows an alternative embodiment of a system 15 that includes several of the components of FIG. 1B. As an alternative to generating the ultrasound trigger pulse or signal directly in the PIU dock 120, the trigger information can instead be transmitted from the imaging engine to the PIU dock along the same optical fiber used to carry the ultrasound image information. The electronic trigger signal can be created by a controller 158 such as microcontroller in the imaging engine 145 and can then be converted to an optical trigger signal with an E/O converter 157b, where the E/O converter wavelength is selected to be different than the wavelength used to carry ultrasound data. The optical trigger signal may then be combined onto the fiber carrying ultrasound image data by use of a wavelength division multiplexing (WDM) filter 160a.

In turn, the trigger signal may then be transmitted to the PIU dock 120, separated from the ultrasound image data by another WDM filter 160b, and converted back into an electrical signal by an O/E converter 122b. This trigger signal may then be passed to the US electronics and trigger generation of an ultrasound pulse. The timing of the electronic trigger may be adjusted by a microcontroller such that ultrasound image data and OCT image data arrive back at the digitizer board 134 in the server 135 at the same time. There are certain advantages associated with using a first WDM filter and a second WDM filter with a reflector or mirror 163. This arrangement has the advantage of reducing the number of optical components required in the PIU dock 120, since only a fixed mirror 163 is required to be in communication with the reference arm instead of a fixed mirror, splitter, circulator, and fiber Bragg grating.

The microcontroller 158 can be configured to generate an electrical trigger pulse that is converted to an optical pulse in the O/E converter 157a. The first WDM 160a is used to merge the trigger pulse onto the same optical fiber carrying the ultrasound image data (which is flowing in the opposite direction). The second WDM 160b in the PIU dock is used to split the optical trigger pulse apart from the optically transmitted ultrasound image data. The optical trigger pulse is converted back to an electrical trigger pulse in the O/E converter 122b, and is then sent to the US electronics in the PIU 115 where it triggers generation of an outgoing ultrasound pulse. In one embodiment, converter 122a is used for the transmission of ultrasound image data from the PIU 115 to the server 135. Converter 122a is linked to converter 157a. The microcontroller is configured to synchronize the transmission of the electrical trigger pulse such that an outgoing ultrasound pulse is created in the PIU at the same time that the first wavelength in an OCT sweep is passing through the PIU 115 on its way to the catheter-based OCT image data collection probe. The microcontroller 158 is linked to the server 135 to allow for updating the microcontroller firmware and changing the delay time settings. In one embodiment, as shown in FIG. 1C, the microcontroller 158 is configured to generate a trigger pulse that it would not otherwise generate if the first and second WDMs 160a, 160b were not incorporated in the embodiment. In addition, in one embodiment, FIGS. 1B and 1C depict various components which include one or more networks that includes links between various primary and secondary components. These links can be optical, or electrical in various embodiments. Electrical links or in electrical communication includes wireless communication or links in one embodiment.

In one embodiment of the imaging engine 145, the interferometer 151 is a Michelson interferometer as shown in detail in FIG. 2A. A portion of light from the light source 147 arrives at a first optical coupler 308 such as for example a 90/10 optical coupler. A fraction of light from one output of the coupler 308 is directed towards a sample arm (SA) 309, while another fraction is directed towards a reference arm (RA) 311. The coupling ratio of the first optical coupler 308 is preferably selected to direct a majority of the light to the sample arm 309 in order to obtain high sensitivity OCT images. In one embodiment, the coupler directs 90% of the light towards the sample arm 309 and 10% of the light towards the reference arm 311.

The reference arm 311 includes a 4-port circulator 317, arranged such that light entering port 1 from the coupler 308 is directed to a reflective variable path length mirror (VPLM) 319 in communication with port 2 of the circulator 317. In one embodiment, the VPLM 319 is controlled by a controller 158. The VPLM 319 can be any reflective device where the light travels through an adjustable optical path to match the path length in the sample arm 309. In one embodiment, the VPLM 319 is formed with a collimating lens, an air gap, and a translatable mirror. Preferably, the VPLM 319 employs retro-reflecting optics, such as an optical corner cube reflector, to reduce sensitivity to misalignment and drift.

Light returned from the VPLM 319 is directed to port 3 of the circulator 317 which is in optical communication with a 1×N optical RA switch 153 (not shown). Here, N is the maximum number of procedure rooms that can be supported by the imaging engine. N can be any number supported by optical switch technology, but is preferably between 2 and 8. Light travels through the reference arm 311 through the RA switch output to the PIU dock (FIG. 1B) 120, which may be located a distance away (about 5 to about 100 meters) in a remote procedure room. In contrast to the present invention, previously-known interferometer designs have confined the entirety of the reference arm to the imaging engine. While this is acceptable for short (less than about 5 meters) distances between the imaging engine and the sample to be imaged, limitations arise when the distance between the imaging engine and the sample to be imaged are long (greater than about 5 meters).

In turn, environmental fluctuations between the imaging engine and the portion of the sample arm not contained in the imaging engine lead to relative changes in optical path length, stress, chromatic dispersion, birefringence, and polarization mode dispersion between the reference arm and sample arm, which results in degradation of image quality and necessitates complex correction software or hardware to be applied. In one embodiment, the majority of the optical paths of the reference and sample arms are exposed to the same environmental conditions, eliminating this problem. The ability to accommodate long optical interconnections between the optical engine and the PIU dock permits flexible placement of the bulky hardware at locations remote from the patient table where the procedure is performed. A portion of the reference light returns from the PIU dock 120 and passes back through the RA switch 153 and is directed to a polarization controller (PC) 323 through port 4 of the circulator 317. The PC 323 is adjusted to match the polarization state of the reference light to the state of the sample light, thereby maximizing the intensity of the resulting interference pattern generated at the 50/50 coupler 327.

The sample arm SA 309 also includes a 4-port circulator, arranged such that light entering from the coupler 308 in port 1 is first directed to a reflective mirror 312 connected to the port 2. The mirror 312, in various embodiments, is a Faraday mirror, a fiber coated with a reflective material, a bulk mirror, or any other reflective structure. Since light in the RA 311 makes three total passes through the circulator material 317, a matching 4-port circulator 310 is used in the SA 309 as well. Light travels from port 3 of the SA circulator 310 and enters a 1×N optical switch 155 (not shown). Light travels from the SA switch 155 output to the PIU dock (FIG. 1B) 120, where it passes through to the PIU 115 and is directed to an imaging catheter via a rotary optical coupler. Instead of a 4-port circulator 310 a 3-port circulator can be used in the SA 309 to reduce transmission losses; however, it would then be necessary to match the total chromatic and polarization mode dispersion of both arms of the interferometer to avoid broadening of the OCT point spread function. Alternatively, a transmissive optical delay line and a pair of 3-port circulators can be used instead of the VPLM and the pair of 4-port circulators 310 and 317.

Light returning from a coronary blood vessel, or other tissue sample, as collected by a forward scanning or side scanning rotatable optical fiber in an OCT probe, passes back through the SA switch 155 and is directed from the fourth port of the SA circulator 310 to the 50/50 coupler 327. The sample and reference light beams combine within coupler 327. The interference pattern is converted to an electrical signal by a balanced detector 328 and is transmitted to a first channel of a digitizer 134 in electrical communication with the server 135.

Figure 2B:
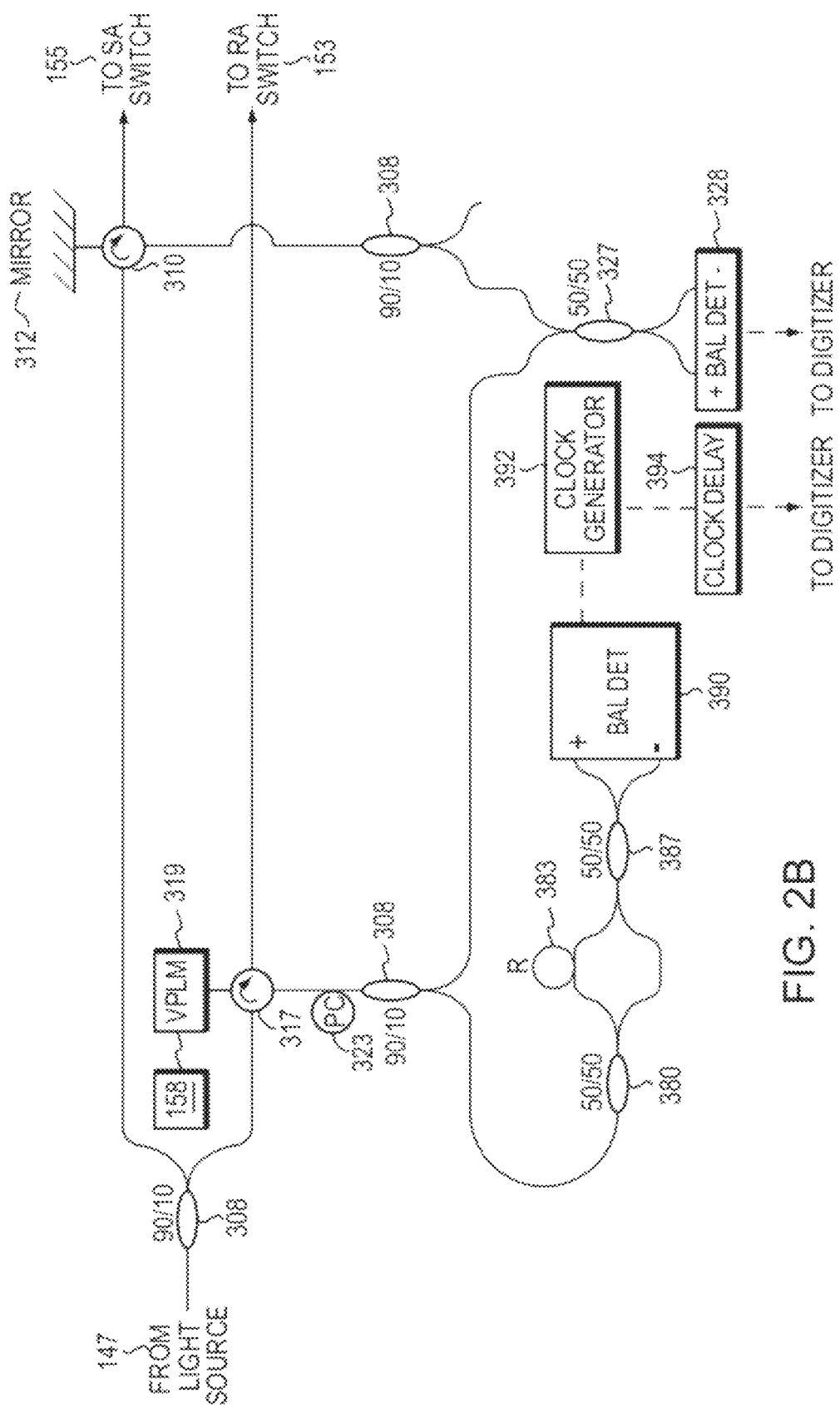
FIG. 2B depicts an interferometer that incorporates an input port for a Mach-Zehnder interferometer in the reference arm of a Michelson interferometer and other components in accordance with an illustrative embodiment of the invention.

Another embodiment of the invention relating to an interferometer as shown in FIG. 2B. In this embodiment, a Michelson interferometer is combined with a MZI. As an alternative method for achieving length matching between the MZI path and the Michelson path, light returning from the remote procedure room in the reference arm of the Michelson interferometer is used as the input to the MZI.

Figure 3:
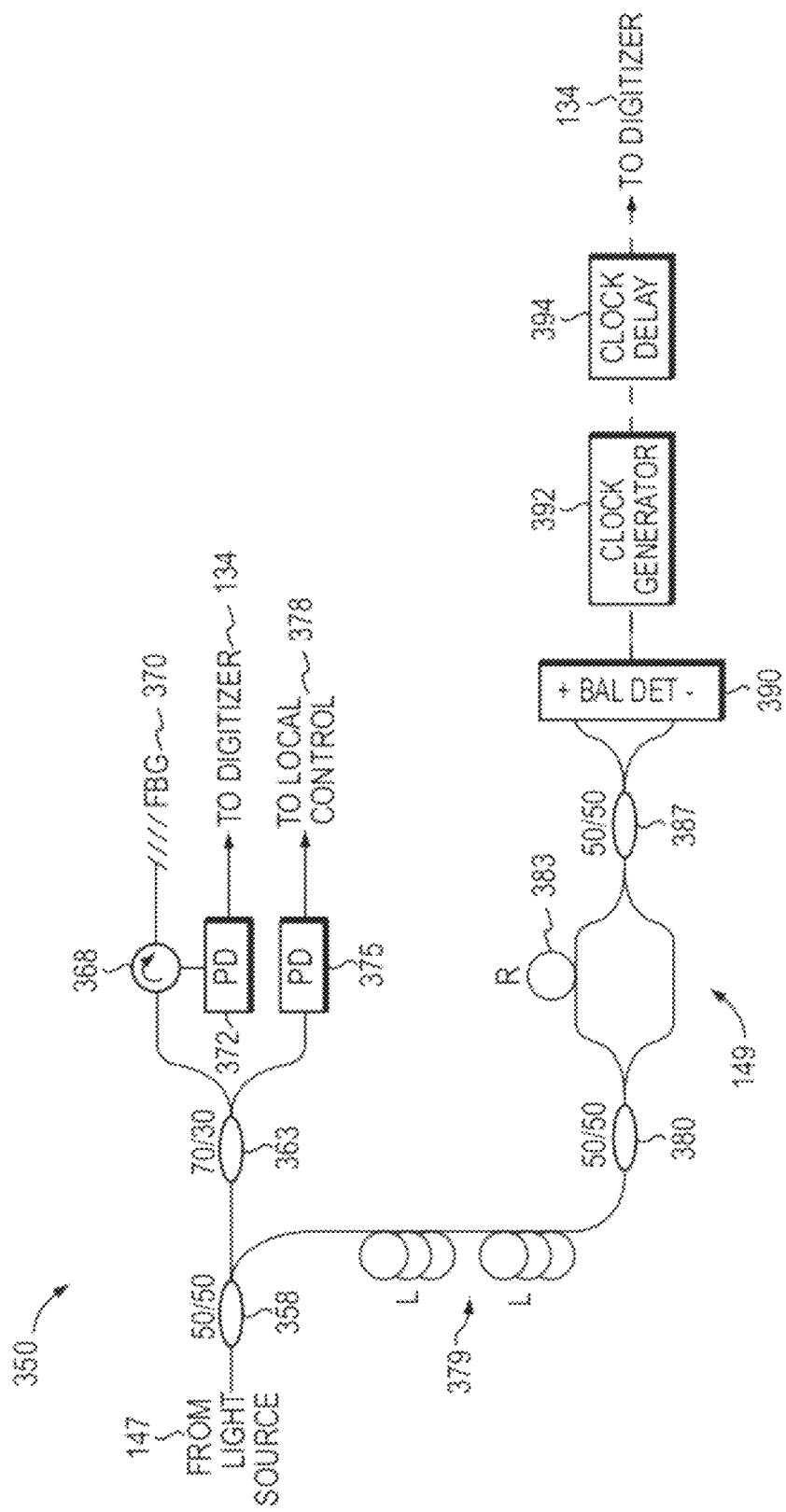
FIG. 3 depicts an opto-electronic subsystem configured to generate one or more signals of interest in accordance with an illustrative embodiment of the invention.

FIG. 2B includes various optical elements that are also used in FIGS. 2A and 3. As shown in FIG. 2B, an optical coupler 308 may be connected to the fourth port of the optical circulator in the reference arm, for example, and may direct 10% of the reference arm light to the input of the MZI.

A second coupler 308 having the same split ratio may optionally be connected to the fourth port of the optical circulator in the sample arm in order to match the spectral transmission characteristics of the reference arm. This configuration is advantageous since another path-matching fiber of length 2L is not required to equalize the time of flight of light in the MZI to that of light in the Michelson interferometer, reducing the size of the overall optical assembly. Additionally, since light travels in a common mode configuration through the reference arm and the MZI until such light reaches the splitter at the MZI input, variations in dispersion between the two interferometers are minimized and the OCT point spread function is not substantially distorted. As shown, loop R corresponds to a small path delay 383 that is used to generate a reference interference fringe where the zero-crossings are uniformly spaced in optical frequency.

Figure 2C:
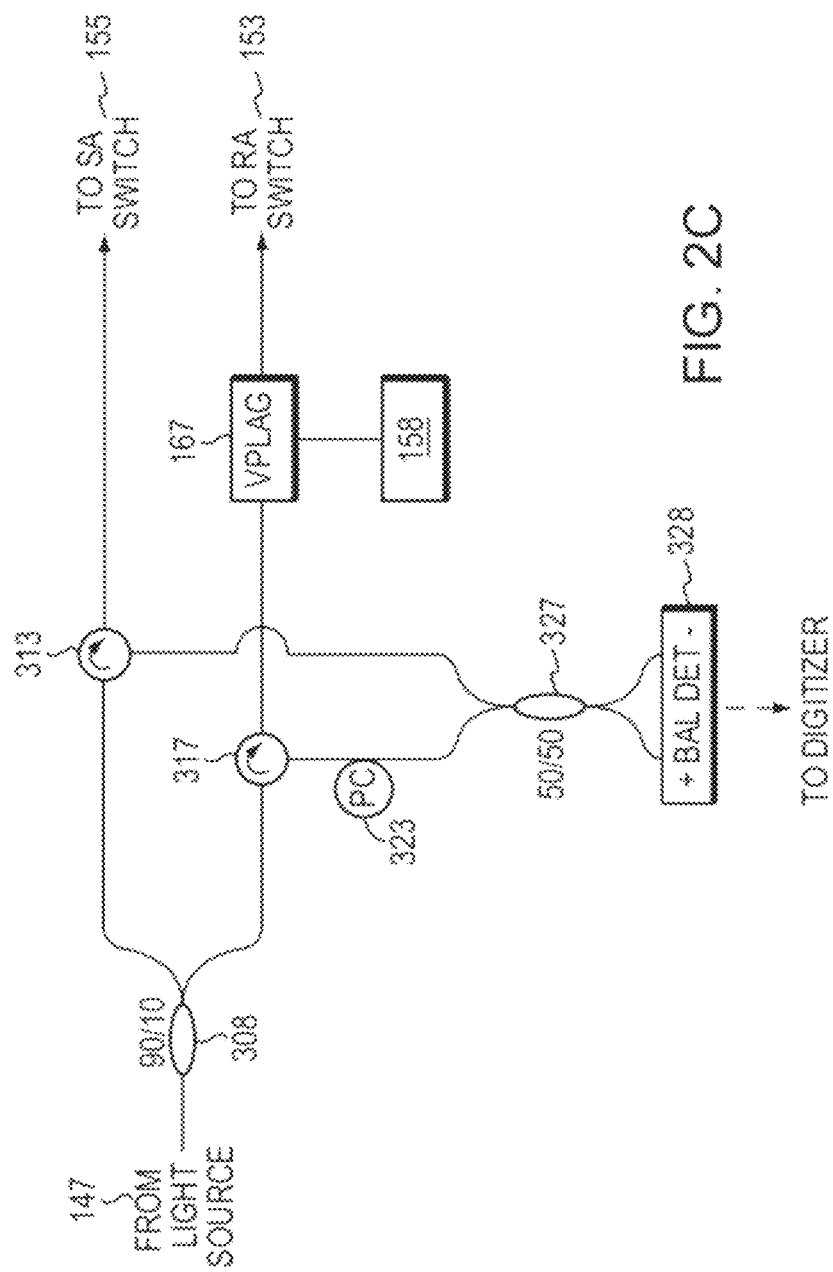
FIG. 2C depicts an interferometer that incorporates a variable path length air gap and other components in accordance with an illustrative embodiment of the invention.

Yet another interferometer embodiment is shown in FIG. 2C. FIG. 2C includes various optical elements that are also used in FIGS. 2A, 2B and 3. In this embodiment, a Michelson interferometer is used with a transmissive reference path. The Michelson interferometer can also be configured to incorporate two three-port circulators instead of two four-port circulators. Two three-port circulators 313, 317 are used in one embodiment. In FIG. 2C, three-port circulator are used such that the mirror shown in embodiment of FIG. 2A is removed.

In this configuration, the variable path length mirror is replaced with a variable path length air gap (VPLAG) 167 that transmits light rather than reflects light. A microcontroller 158 is in electrical communication with the VPLAG 167. Thus, the path length of the VPLAG 167 changes over time in response to input control signals from the microcontroller 158. In one embodiment, the VPLAG 167 includes two collimating lenses and air gap wherein one lens is mounted on a motor such that when the motor is actuated the air gap changes. The VPLAG 167 can be controlled by the microcontroller 158. This configuration is advantageous since three-port circulators are less expensive and suffer from lower insertion losses than four-port circulators, although transmissive air gaps are more prone to misalignment and drift than reflective systems. The VPLAG 167 can be located in the remote procedure room, such as in the PIU dock or PIU. It is also understood that a reflective VPLM could be located in the PIU dock or PIU.

Exemplary details of the MZI 149 and auxiliary electro-optical circuits of an imaging engine embodiment 145 are shown in FIG. 3. FIG. 3 depicts an opto-electronic subsystem 350 suitable for generating one or more signals of interest such as a k-clock, sweep trigger, and intensity monitor. A portion of light from the light source 147 arrives at an optical coupler 358 and is split by the optical coupler 358 into two fractions. One fraction of light from the coupler 358 is directed towards the MZI 149, while another fraction is directed towards another optical coupler 363. The coupling ratio of the first optical coupler 358 is preferably selected to direct equal amounts of light to the MZI 149 and the second optical coupler 363. Light entering the second optical coupler 363 is in turn split into two other portions. One portion is directed through a 3-port circulator 368 to a fiber Bragg grating (FBG) 370 and the other portion is directed to photodetector 375.

The FBG 370 reflects only a narrow bandwidth of the incident light at a known wavelength, such that an electronic pulse is generated by the photodetector 372 each time the light source 147 sweeps through the known wavelength. A time-delayed version of this pulse is transmitted to the digitizer 134 and is used to trigger acquisition of individual image line data from an OCT probe positioned using a catheter and coupled to a PIU. A second portion of light output from the second optical coupler 363 is directed to a photodetector 375 that produces a time-resolved intensity trace of the light source emission. This signal is returned to a local controller 378 inside the imaging engine 145 for controlling parameters such as the light source intensity.

The second fraction of light exiting the first optical coupler 358 enters a fiber-optic delay line 379 having length 2L, where L is equal to the length of the cables 136, 137, 138, 139 connecting the imaging engine 145 and server 135 to the PIU dock 120. The path length of the delay line 379 must be matched to the connecting cables 136, 137, 138, 139 in order to ensure synchronization between the clock signal generated from the interference pattern generated by the MZI 149 and the interference pattern generated in the Michelson interferometer 151. In embodiments of this invention where the PIU dock 120 is located remotely from the imaging engine 145, L is the main contributor to the overall optical path length of the system. Still, it is understood that the complete path lengths of the Michelson interferometer 151 and MZI 149 must be matched from the point where light is directed out of the light source 147 to the point where the resulting electronic signals are received by the digitizer board 134. In one embodiment, the path lengths are also matched for electrical signals. L should be at least 5 meters long to allow a cable to be run from a control room to a procedure room. Preferably L should be at least 30 meters long to allow connection of multiple procedure rooms to a main control room. In some settings L should be at least 100 meters long if the procedure rooms are separated by long distances or are located on different floors of a building.

After passing through the 2L delay line, the light enters the first coupler 380 of a standard MZI 149 with a path imbalance R 383. The MZI interference pattern in the second coupler 387 is converted to an electronic signal by a balanced detector 390, and a series of pulses at evenly spaced optical frequency intervals is generated by a clock generator 392 to form the k-clock pulses. Here, "k" refers to the commonly-used symbol for optical frequency. Path imbalance R 383 is selected such that the MZI 149 generates interference fringes at a frequency corresponding to the desired OCT system imaging depth, taking into account any electronic clock rate modifications in the clock generator circuit and correcting for the refractive index of the optical fiber. For example, if the desired OCT imaging range is about 10 mm in air and one k-clock pulse is generated during each MZI interference fringe cycle, then R should be (4×10 mm)/1.4676 or about 27.3 mm. If, for example, the k-clock frequency is quadrupled electronically in the clock generator circuit, then R should be about 6.8 mm.

After the k-clock signal is generated, the overall time delay and individual spacing of the k-clock pulses can be adjusted in the clock delay circuit 394. The purpose of this circuit is to compensate for residual path length mismatches between the MZI 149 and Michelson interferometer 151, and to compensate for dispersion imbalances between the reference arm and sample arm of the Michelson interferometer 151. Although the optical fibers in the reference arm and sample arm are configured to minimize these imbalances, slight differences in the core sizes and the stresses applied to the fibers give rise to chromatic dispersion and polarization dispersion, which can degrade the resolution of OCT images.

To reduce dispersion-induced image degradation, the spacing between the edges of the pulses generated by k clock during the laser sweep interval can be altered. Thus, in one embodiment the interval is adjusted slightly such that the OCT interference signal is sampled at the proper times to compensate for residual wavelength-dependent optical group delay.

Figure 4:
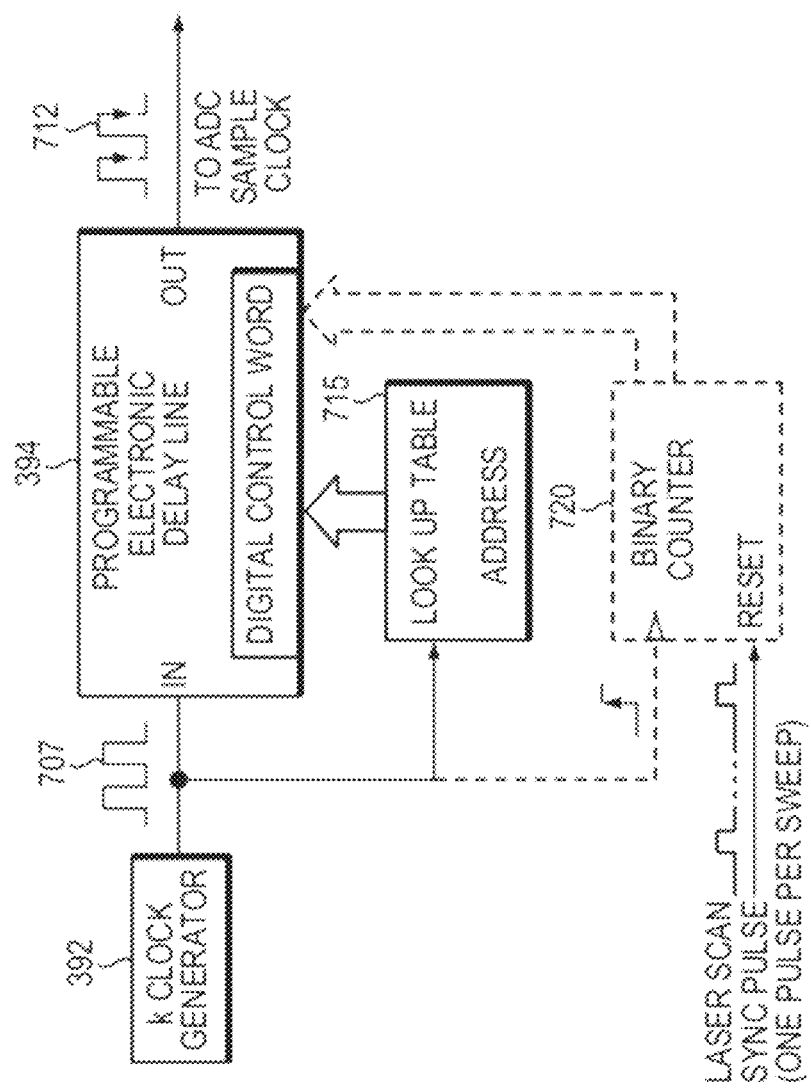
FIG. 4 depicts a block diagram of an embodiment of a digital clock in accordance with an illustrative embodiment of the invention.

FIG. 4 depicts an embodiment of a digital clock generator that allows adjustment of the intervals between k-clock pulse edges according to a preset or feedback controlled profile. In one embodiment, the clock generator 392 enables dynamic adjustment of the intervals between k-clock edges according to a sequence of control words stored in a look-up table. Each value of the look-up table is a digital word that sets the interval by which a given pulse edge is delayed relative to the preceding pulse edge. This embodiment of the clock generator includes a programmable electronic delay line 394 in which the binary control word that sets the delay interval is loaded from a look-up table 715. In one embodiment, light from light source resets the counter. In one embodiment, the k clock sets the clocking for the counter.

To set each delay interval between the output clock edges on which the OCT signal is sampled by the analog-to-digital converter (ADC), a new control word is loaded on the leading edge of each input clock pulse. Between successive falling edges of the delayed pulse train, there is a time interval. This time interval increases or decreases according to the sequence of control words stored in the look-up table. In this manner, a delay curve of an arbitrary shape can be superimposed on the k-clock. Typically, compensation of small amounts of residual dispersion can be accomplished with a polynomial curve described by a few coefficients. If only a linear delay profile is required, the look-up table 715 can be replaced with a simple binary counter 720.

Figure 5:
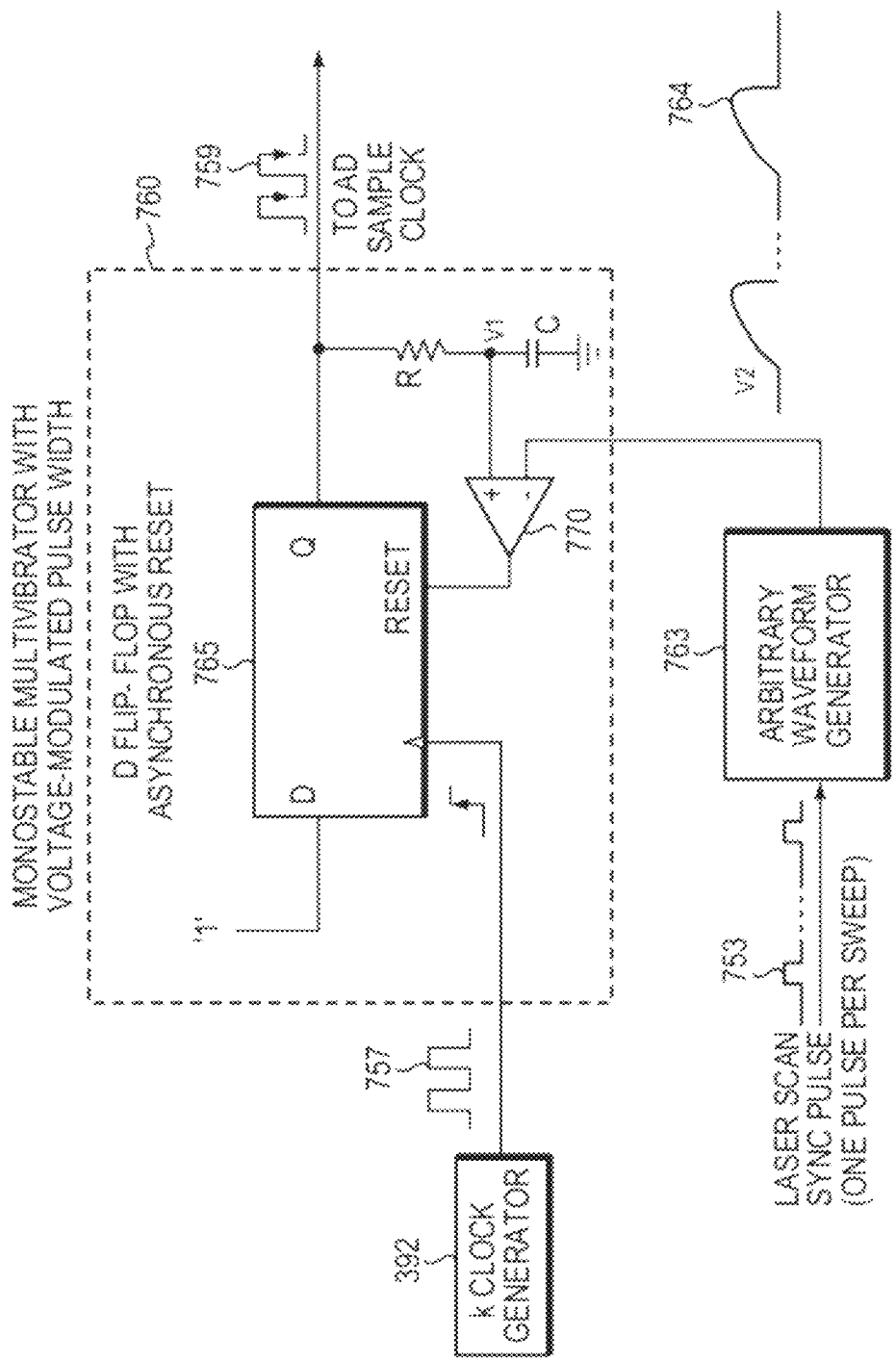
FIG. 5 depicts a block diagram of an alternative embodiment of clock generator in accordance with an illustrative embodiment of the invention.

FIG. 5 shows an alternative configuration of a digital clock generator 392 based on a subsystem 760 that includes a monostable multivibrator with voltage-modulated pulse width. This subsystem 760 employs a voltage-adjustable pulse width or arbitrary waveform generator 763 to set the intervals between the k-clock edges. The generator 392 is in electrical communication with a monostable multivibrator 760. The generator can be a function generator or other suitable waveform selectable generator. This clock generator embodiment enables dynamic adjustment of the intervals between k-clock edges according to the shape of an applied waveform. In this embodiment, the output of the k-clock generator 392 is an input to a monostable multivibrator 765 that can be implemented using a flip-flop component with the D input held at 1. The output of a comparator 770 resets the flip-flop of the monostable multivibrator 765. The inverting input of the comparator 770 is connected to the output of an arbitrary waveform generator 763 which is triggered by a laser scan pulse 753. The laser scan pulse, derived from the FBG synchronization signal 372 in FIG. 3, for example, initiates the generation of the arbitrary waveform at the beginning of each laser scan.

If a threshold voltage V2 is applied to the inverting terminal of comparator 770 and is held constant, the width of the pulse produced by the monostable multivibrator 765 is determined by the time required to charge capacitor C through resistor R. However, when V2 from the output of the arbitrary waveform generator 763 varies in time, the pulse width varies dynamically in synchrony with the laser sweep. The OCT image resolution is optimized by adjusting the coefficients of a polynomial function that defines the waveform such that the width of the point-spread function of the OCT system is minimized. This adjustment can be accomplished manually by trial and error or by computer according to a programmed optimization routine.

Figure 6:
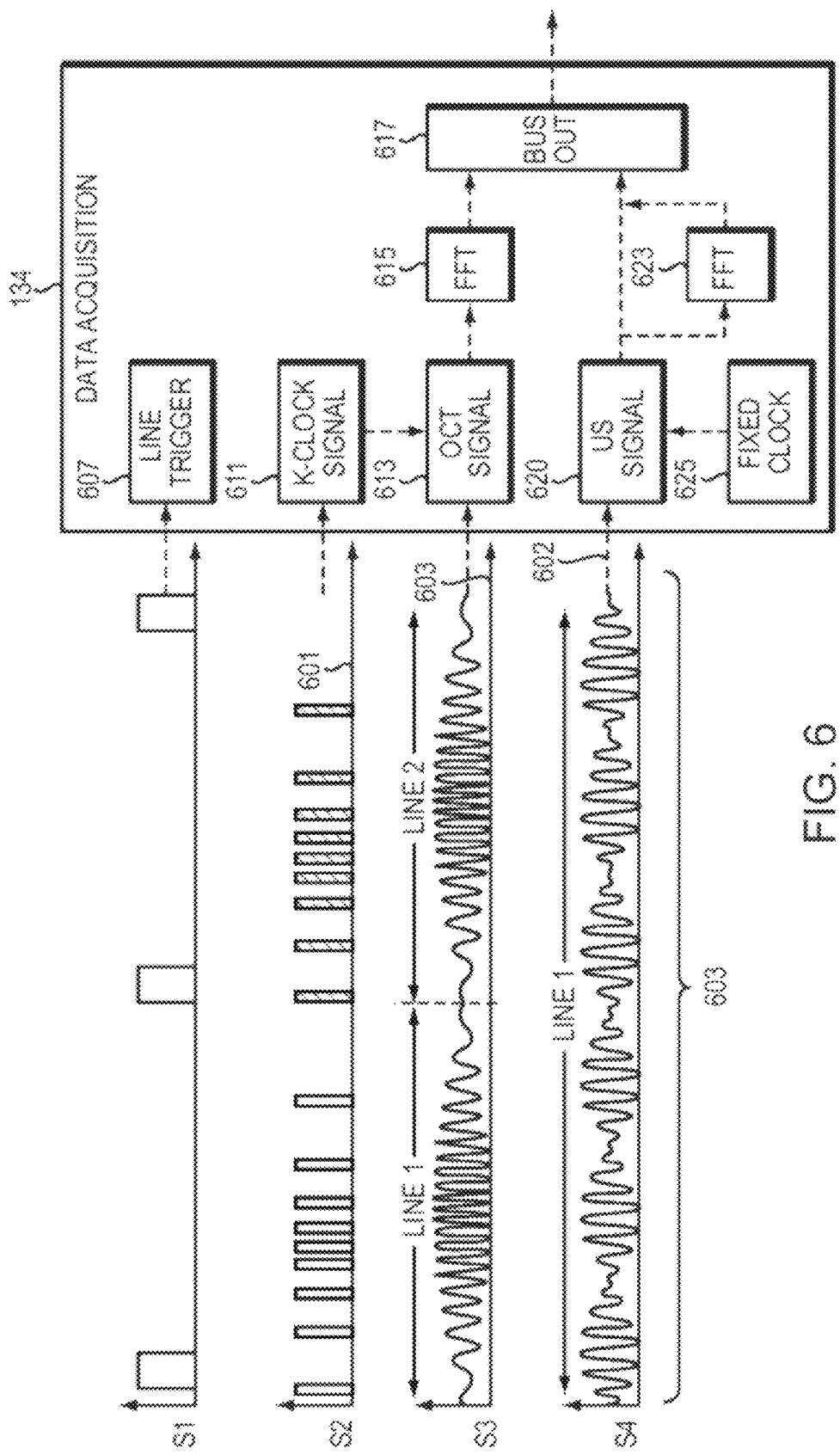
FIG. 6 depicts a schematic diagram and timing signals for an embodiment of a multi-channel data acquisition device used in accordance with an illustrative embodiment of the invention.

An exemplary embodiment of the multi-channel digitizer or device 134 that samples the OCT and ultrasound signals in the server 135 is shown in FIG. 6. In one embodiment, the 134 is configured for simultaneous, asynchronous sampling of optical coherence tomography and ultrasound signals. At least one channel of the digitizer 134 is dedicated to OCT signal acquisition. In one embodiment, at least one other channel is dedicated to ultrasound signal acquisition. It is understood that additional channels can be used for specialized types of OCT imaging, such as polarization-sensitive OCT. The sweep trigger generated by the photodiode 372 in communication with the FBG 370 in the MZI 149 occurs at a fixed wavelength position during each scan. By applying a fixed delay time to the sweep trigger, the pulse can be shifted to occur at the starting point of each OCT and US image line and can therefore be used as a line trigger that initiates acquisition of each OCT and US image line.

Because the number of image lines generated per second may be different for the OCT and ultrasound components of a multimodal image data collection system, the digitizer 134 may be configured to downsample the sweep trigger on one acquisition channel. For example, the OCT components may generate 200,000 image lines per second whereas the ultrasound components may generate 100,000 images line per second. Since the sweep trigger is also generated at a rate of 200,000 pulses per second, the digitizer 134 may be configured to ignore every second sweep trigger pulse for acquisition on the ultrasound channel.

In addition to the sweep trigger, the digitizer 134 also receives the digital k-clock pulse train that triggers acquisition of each sample of the OCT interference signals. In FIG. 6, the k-clock signal S2 or 601 is shown as a group of unevenly spaced pulses. Pulses corresponding to one OCT sweep are shown as clear boxes, and pulses corresponding to the subsequent OCT sweep are shown as hatched boxes. Although only a small number of k-clock pulses is shown, it is understood that up to several thousand samples may be acquired during each OCT sweep. The ultrasound signals S4 or 602 are acquired using a fixed-frequency sample clock generated internally by a crystal oscillator 625 located on the data acquisition card. In FIG. 6, for illustrative purposes only, the ultrasound line rate S4 is shown as being 50% of the OCT line rate 603 or S3.

In the embodiment shown the digitizer 134 may be configured to perform fast Fourier transforms (FFT) on the OCT channel and/or the ultrasound channel using a field programmable gate array (FPGA), digital signal processing (DSP) chip, application-specific integrated circuit (ASIC), or other digital logic device 615, 623. In FD-OCT systems, it is necessary to perform an FFT prior to forming tomographic images. An FFT step is not required to form conventional ultrasound images, although an FFT may be applied to conduct frequency analysis of the ultrasound data.

Additional signal processing steps such as logarithmic scale compression and digital filtering may also be incorporated onto the data acquisition device, such as for example, a digitizer as described herein, to reduce the burden on the server. After data acquisition and FFT processing, the OCT and US image lines are buffered, re-synchronized, and transmitted by a bus chip 617 to the computer's signal bus. The lines are stored in system memory for further processing and conversion to OCT and IVUS images.

In one embodiment, the imaging engine 145 can also contain components for receiving and converting ultrasound data transmitted from the PIU dock 120. Because ultrasound signals of the type used for intravascular imaging typically occupy a portion of the frequency spectrum from 0 Hz to less than about 200 MHz, these signals can be converted to optical signals and transmitted over long distances without degradation using multimode or single-mode optical fiber. The optical signal is passed between the imaging engine 145 and the PIU dock 120 through the 1×N optical US switch 159. The output of the switch 159 (FIG. 1B) is connected to the optical to electrical (O/E) converter 157, which converts the optical signal back into an electronic form. The O/E converter 157 can be a simple photodetector with a transimpedance amplifier. The electrical rendition of the ultrasound signal is then directed to a second channel of a digitizer 134 in the server 135.

The O/E converter 157 in the imaging engine and the E/O converter in the PIU dock are in optical communication with each other via an optical fiber as shown in FIG. 1B. In one embodiment, US signals are collected using a US probe and transmitted using a conductor such as a wire with suitable shielding. In other embodiments, as shown in FIG. 1B all of the data collected using OCT or US is transmitted by a plurality of optical fibers. Three optical fibers for the sample arm, the reference arm, and the US optical signal are shown in FIG. 1B. Although some of the lengths in the figures are shown as L, the lengths can be the same or different in various embodiments.

A laser diode or other light source in the E/O converter 122 can receive an input radio frequency or other type of signal from the US probe and modulate the light source in the E/O converter. The modulation can be digital or analog. In a preferred embodiment, the modulation is analog. The optical signal from the converter 122 includes the US data from a US probe. This optical signal is transmitted to the other converter 157 where the optical signal is converted back to an electrical signal for transmission to the server. This paired system of an optical to electrical converter, an optical fiber, and an electrical-to-optical converter reduces the need for shielding and avoids degradation of the US signal by electrical attenuation or dispersion in long electrical transmission lines and electromagnetic interference from external devices.

The PIU dock 120 serves both as a mechanical mount for the PIU 115 when the PIU 115 is not in use, and as an opto-electrical interface between the PIU 115, control panel 133, imaging engine 145, and server 135. The PIU dock 120 can include reference optics 121, an electro-optical converter 122, a digital link hub 123, wireless pressure or FFR data receivers 129, 130, and circuitry 127 for electronic communication with the PIU.

Figure 7A:
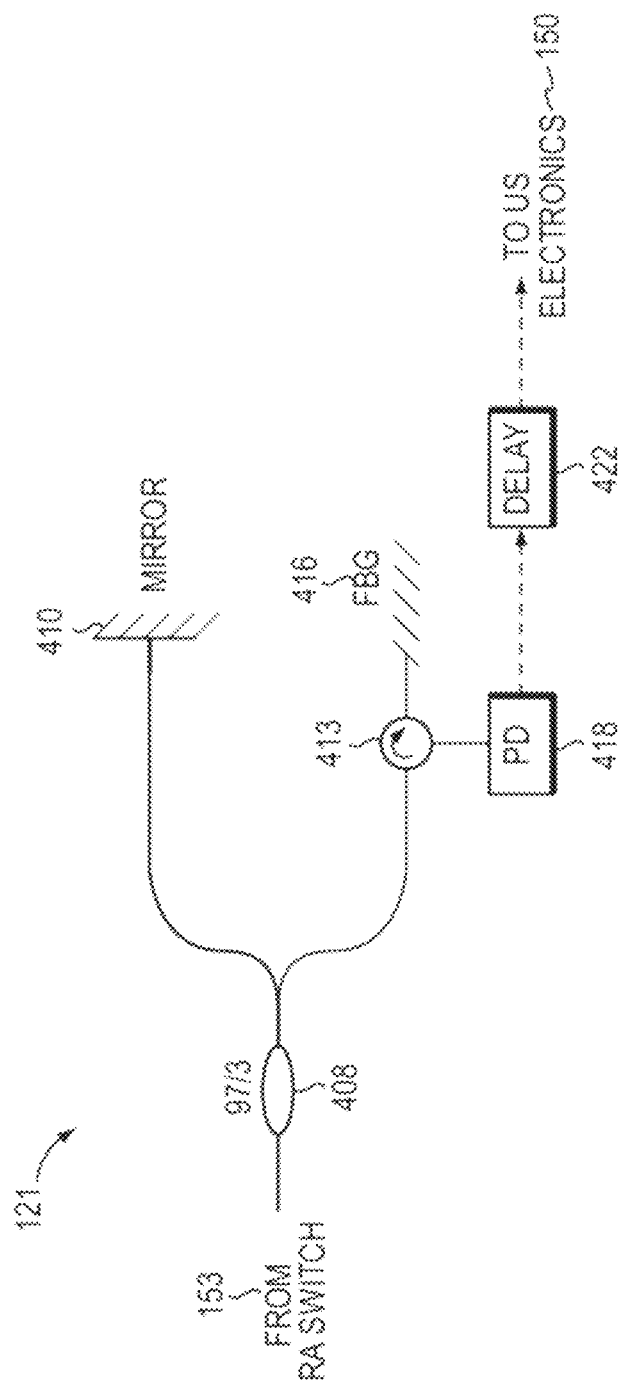
FIG. 7A depicts an embodiment of exemplary reference optics of a patient interface unit (PIU) dock in accordance with an illustrative embodiment of the invention.

Exemplary reference optics 121 of the PIU dock 120 are shown in FIG. 7A. An optical coupler 408 directs a fraction of light received from the reference arm switch 153 towards a fixed mirror 410, while another fraction of light is directed towards a circulator 413 such as a three-port circulator. The coupling ratio of the optical coupler 408 is preferably selected to direct the majority of light to the fixed mirror 410. The fixed mirror 410 in various embodiments is a Faraday mirror, a fiber coated with a reflective material, a bulk mirror, or any other reflective structure. This mirror 410 forms the terminal end of the Michelson interferometer reference arm 311. Placing the terminal end of the reference arm 311 in the PIU dock 120 ensures that the light undergoes substantially the same environmental variations while traveling through the reference arm and sample arm, except for the portion of the sample arm located in the PIU 115 and imaging catheter or probe.

To facilitate the generation of ultrasound pulses synchronously with exposure of the sample tissue to OCT light, the PIU reference optics 121 includes, in one embodiment, a circulator 413, a Fiber Bragg Grating (FBG) 416, and photodetector 418 configured to send a pulse transmit trigger to the ultrasound electronics 150 in the PIU 115. The FBG 416 reflects light over a narrow range of wavelengths, and is selected to reflect the same narrow range of wavelengths as the FBG 370 (FIG. 3) located in the imaging engine 145. For example, in an embodiment as shown in FIG. 7A, the FBG 416 is selected to reflect a narrow range of wavelengths at the center of the spectrum of the OCT light. The photodetector (PD) 418 generates an electrical pulse at a time corresponding to the center of the light source sweep.

Figure 7B:
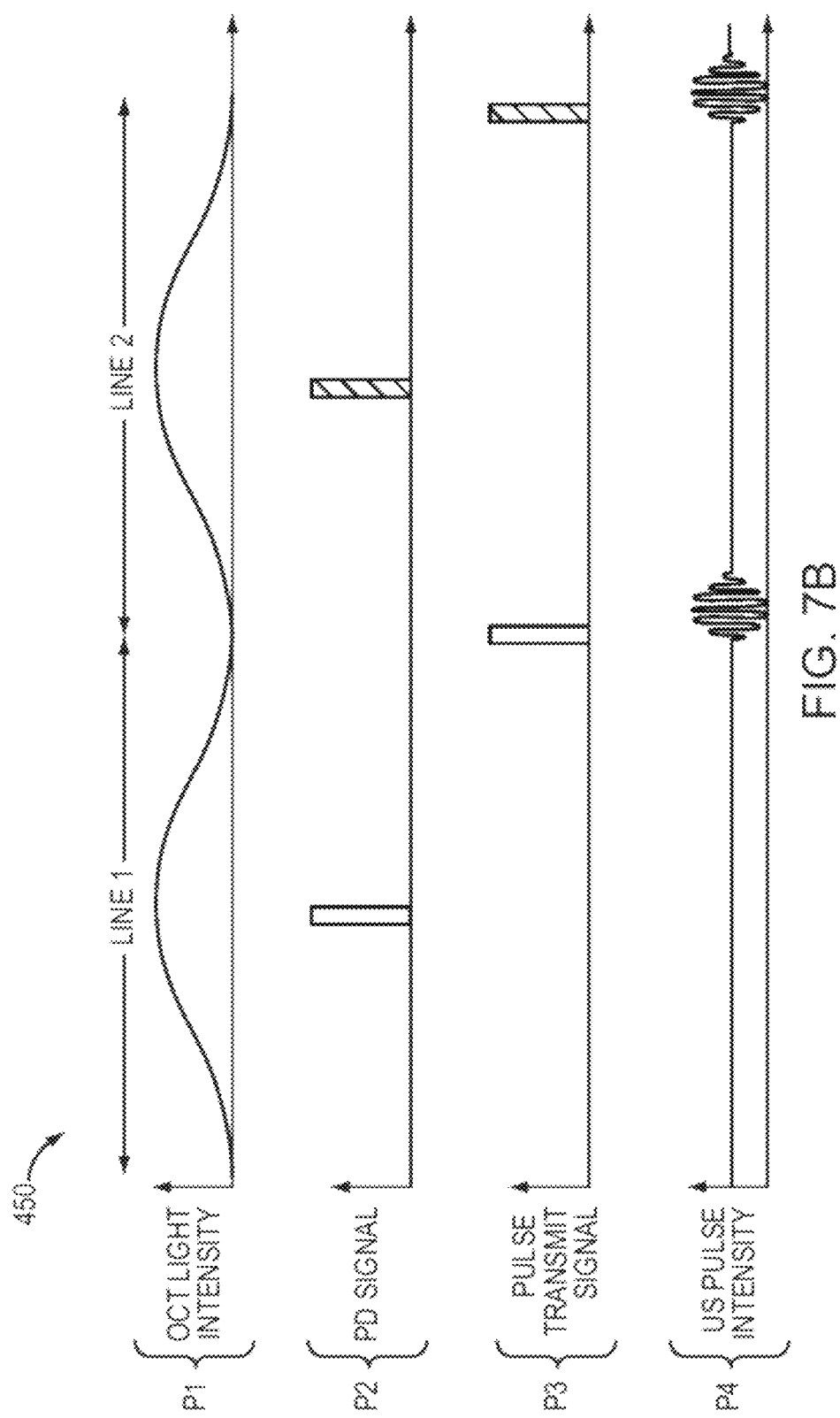
FIG. 7B depicts a relationship of multiple signals associated with the reference optics shown in FIG. 7A in accordance with an illustrative embodiment of the invention.

In addition, as shown, a programmable delay circuit 422 is configured to delay this pulse by approximately ½ of the sweep period, such that the resulting ultrasound pulse transmit signal occurs at the beginning of the subsequent light source sweep. An ultrasound pulse P4 is generated from a transducer when the ultrasound control electronics receive the pulse transmit signal P3. This is shown in FIG. 7B, where the pulse transmit signal P3 from the first OCT line is shown as a clear pulse and is a time-delayed version of the corresponding PD signal P2, also shown as a clear pulse, from the first OCT line. The subsequent pulse transmit signal P3, aligned to the second OCT line, is a time-delayed version of the corresponding subsequent PD signal P2, where both are shown as hatched pulses. In this way, ultrasound pulses P4 are generated by the transducer at the tip of the US imaging probe at the same time that OCT light illuminates the sample, thereby preventing mis-synchronization of OCT and ultrasound image data.

The PIU dock 120 can also incorporate the digital communication hub 123 (FIG. 1B), whereby a single digital link 136 to the server 135 is split into multiple ports. Any suitable digital link, such as Ethernet, can be used. In one embodiment, the digital link can for example be an optical USB link and the hub can be a USB hub. Use of a single link, multi-port hub architecture minimizes the number of cables required to connect the server computer to the PIU dock 120.

As shown in FIG. 1B, one port of the hub is used as an interface between the PIU motor drive circuitry 161 and the server 135. In one embodiment, PIU communication circuits 127 are used to reformat control commands sent from the server 135 to the PIU 115. A second port of the hub 123 is used to connect a wireless receiver 129 that receives pressure data from an aortic pressure monitor 129. A third port of the hub is used to connect a wireless receiver 130 that receives pressure data from an invasive pressure wire. In this way, wireless FFR measurements can be made and transmitted to the server 135. Other pressure data-based measurements and parameters can also be determined and sent to the server.

A fourth port of the hub 123 is connected to the control panel 133. The control panel 133 may be a touch-sensitive display device; a series of discrete buttons and switches; or both a touch-sensitive area and a series of discrete buttons and switches. The control panel 133 may also incorporate an input or pointing device such as a track pad, mouse, joystick, roller ball, stylus, or other pointing device known in the art. The control panel 133 may be used to control operation of the complete diagnostic system, and may be mounted in the procedure room or be movable as a mobile terminal. The control panel 133 may include a wireless mouse and a mouse pad, in wireless communication with the PIU dock 120. Additional hub ports may be provided to allow connection of external digital devices, such as portable storage devices or additional diagnostic devices.

The PIU 115 is configured to interface with an OCT imaging catheter or probe, an IVUS imaging catheter or probe, and/or a catheter or probe capable of conducting both OCT and IVUS imaging. The PIU 115 contains a rotary coupler 152 that transmits optical signals, electrical signals, or both. A portion of the sample arm of an interferometer is disposed in part of the patient interface dock in one embodiment and in the patient interface dock and patient interface unit in another embodiment. Motor drive electronics 161 receive control commands from the server 135 that have been routed through the PIU dock 120. The motor drive electronics 161 control motors that produce rotary and linear motion, thereby spinning and pulling back or advancing the imaging or data collection catheter/probe. The PIU 115 in one embodiment also contains ultrasound electronics 150. These ultrasound electronics can be an ultrasound system that can be configured to perform one or more of the following: generating ultrasound pulses, receiving ultrasound signals returned from the sample, and switching the device between transmit mode and receive mode. Locating the ultrasound electronics 150 in the PIU 115 is advantageous for reducing losses and dispersion between the pulse generator and the ultrasound transducer, and reducing electromagnetic interference effects.

In accordance with one embodiment of the invention, OCT light travels between the imaging engine 145 and the PIU dock 120 over two optical fibers 137, 138 of length L, or other lengths, with one fiber carrying reference arm light and the other fiber carrying sample arm light. In one embodiment, the two optical fibers are single-mode fibers, such as Corning SMF-28e or an equivalent. The two fibers are arranged side-by-side in a common cable enclosure. This arrangement is beneficial for reducing the effects of environmental fluctuations on the OCT interferometer. Changes in temperature induce changes in optical path length of optical fiber. If the path length of one arm of the Michelson interferometer changes relative to the other arm, the OCT images will appear to shift in the axial direction. As a result, under such circumstances images of a sample of interest will be distorted. Enclosing the two optical fibers in a common cable enclosure also reduces the differential effects of stress, chromatic dispersion, birefringence, and/or polarization mode dispersion caused by environmental fluctuations, which in turn reduces degradation of OCT image quality.

By co-locating the fibers in a common cable such as a jacket or insulating sheath, temperature fluctuations in the cable will cause substantially the same path variation in the reference and sample arms of the Michelson interferometer. The path variations will therefore cancel one another, and the appearance of the OCT images will not be altered. In addition, local stresses caused by bending and twisting of the cable will be substantially the same in both fibers. This arrangement reduces differential polarization rotation and polarization mode dispersion in the two arms of the Michelson interferometer 151, which can degrade OCT image quality. Although the drawings explicitly show only the cable portions having a path length of L, the complete path lengths of the reference arm and sample arm in the Michelson interferometer 151 are matched in one embodiment to perform OCT imaging.

FIG. 8A shows a cross-section of a cable assembly that can be used to connect the control room to a procedure room. In this embodiment, three optical fibers 510 used to transmit the sample arm light, reference arm light, and optically-converted ultrasound signal are placed inside of a common cable or jacket 512. A fourth optical fiber 505, used as the optical digital link between the server 135 and PIU dock 120, may be placed in a separate cable or jacket 507. The optical digital link may require additional optical fibers, which may also be disposed within the jacket 507.

In those situations in which system power is provided by the imaging engine 145 to the PIU dock 120 and PIU 115, two additional electrical conductors 523 may be placed within an inner jacket such as for example separate braided shield 522 to supply power. The entire assembly may be enclosed in a common protective sheath such as an outer cable or jacket 503 to provide environmental protection. A cross-section of an alternative cable assembly is shown in FIG. 8B. This assembly can be used when system power is available in the procedure room. In this case, the cable assembly is entirely optical, no metal conductors such as copper wire are disposed within the cable assembly, and is immune from electromagnetic interference and electrical hazards. In other embodiments, conductive elements such as metal wires can be disposed in the protective sheath to supply power or transmit electrical signals. In one embodiment, for a given cable embodiment one or more of the optical fibers can be used for data transmission, one or more conductors can be used for electrical power transmission, and one or more mechanical strength members are disposed within a common protective sheath.

Figure 8C:
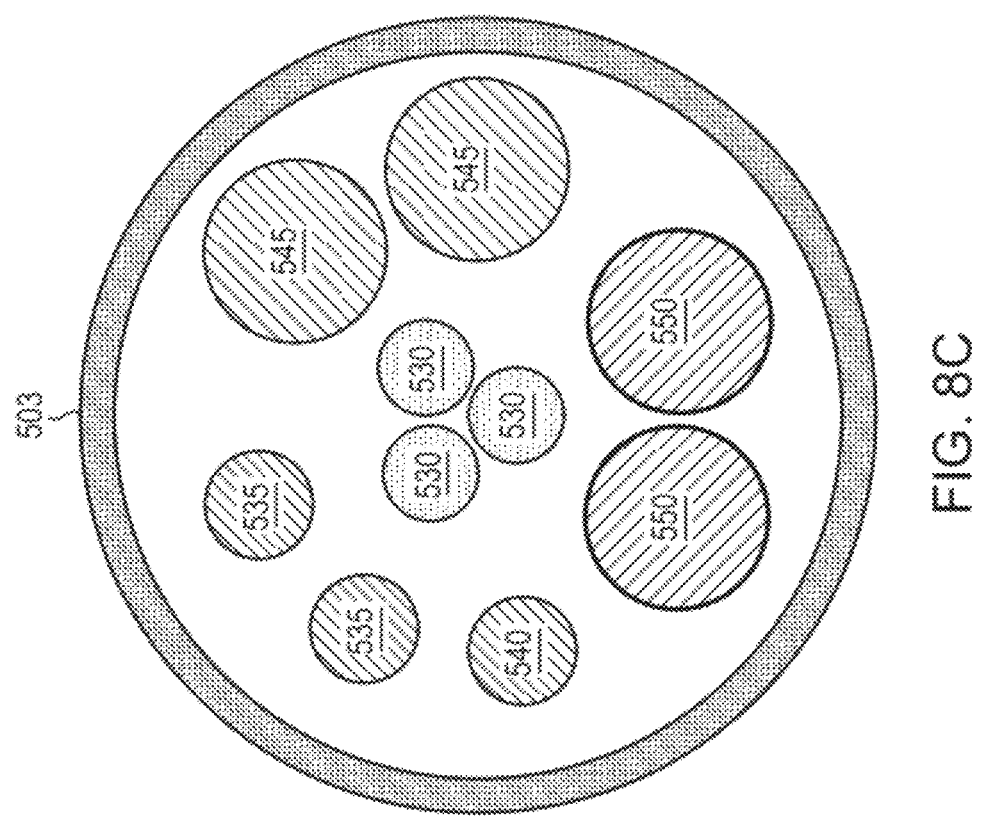

Alternatively, all optical fibers and electrical conductors may be disposed along with mechanical strength members, such as aramid yarn or Kevlar fibers, within an outer jacket 503 without the use of inner jackets 512, 522, and 507. An example of such an embodiment is shown in FIG. 8C. As shown, an outer jacket 503 defines an interior cavity that can include various optical and electrical conductors and strength members 530. Various optical fibers configured to carry OCT data 535 are shown. An optical fiber configured to transmit ultrasound data 540 can also be disposed within outer jacket 530. One or more digital communication fibers 545 can be used to carry suitable data, such as control signals, or other digital information. In addition, one or more electrical conductors 550 can also be disposed within outer jacket 530. The various optical fibers can be single mode or multimode as applicable for a given application.

Figure 9:
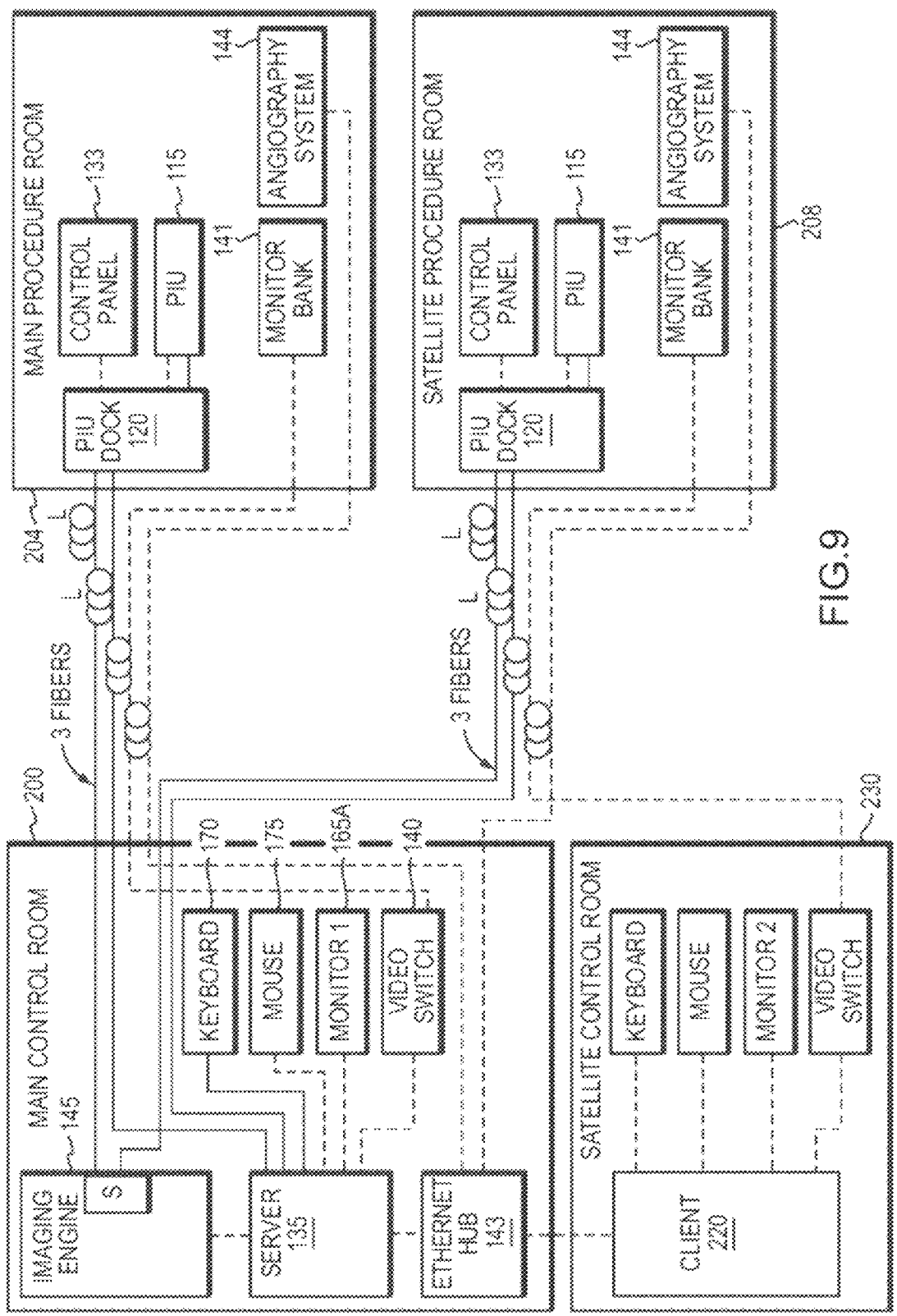
FIG. 9 depicts a block diagram of an embodiment of a multimodal data collection system configured to support multiple procedure rooms in accordance with an illustrative embodiment of the invention.

In many interventional cardiology settings, each procedure room is adjacent to a dedicated control room. Physicians, nurses, and technicians work in teams split between the procedure room 204 and its associated control room 200. FIG. 9 shows a simplified block diagram of the system components configured for imaging in multiple procedure rooms using a single imaging engine 145 and server 135. Major electrical connections are shown as dashed lines, and major optical connections are shown as solid lines. The optical switching network (S) in the imaging engine 145 incorporates the SA switch 155, RA switch 153, and ultrasound (US) switch 159 shown in FIG. 1B. All connections between the main control room 200 and the procedure rooms 204, 208 are the same as the connections shown in FIG. 1B.

A satellite procedure room 208 may be linked to the imaging engine 145 and server 135 in the main control room 200 with a cable assembly of length L containing the same type and number of optical fibers and/or electrical conductors found in the cable assembly linking the main control room 200 to the main procedure room 204. The satellite procedure room interfaces to the imaging engine 145 through the switching network (S), and interfaces to the server 135 through a digital optical link. Even when the diagnostic system is in use in the satellite procedure room 208, all data acquisition and signal processing tasks are conducted in the server 135. Processed diagnostic data including OCT images, IVUS images, FFR data, and angiographic data is passed from the server 135 to a client computer 220 in a satellite control room 230 over a data network.

The client computer 220 receives processed diagnostic data from the server 135 and directs the data to a monitor bank 141 in the satellite procedure room 208. The processed data may be routed through a video switch 140. Because certain aspects of diagnostic system operation are often controlled by personnel in the control room instead of or in addition to personnel in the procedure room, it is also desirable to provide control mechanisms for the diagnostic system in each satellite control room 230. To this end, the client computer 220 is provided with a keyboard, mouse, and monitor in each satellite control room 230. The client computer 220 can thereby send control signals to the diagnostic system over the data network. In the case where two users attempt to assert control of the system at the same time, the server 135 may assign priority to the user who began the procedure first or who is at a more critical phase of the procedure, such as actively acquiring OCT or IVUS or FFR data.

In addition to OCT and ultrasound images, angiographic X-ray images typically provide planar visualizations of vascular morphology over a large field of view. OCT and ultrasound images typically provide cross-sectional visualizations or three-dimensional renderings of vascular microstructure in a single blood vessel over a pullback distance of about 5-about 15 cm. Because interventional procedures such as stent implantation are guided in real time under angiography alone, it is desirable to precisely co-register the large field of view, low-resolution angiography images with the small field of view, high-resolution OCT or ultrasound images. This provides the physician with both contextual data about the overall vascular map and cross-sectional detailed data about the target lesion.

As described above, the multimodal diagnostic system is capable of retrieving previously acquired angiography images by interfacing to a data network that is also connected to an angiographic X-ray system or by interfacing directly with the angiographic X-ray system. The data network may be for example a network associated with a facility operating a catheterization lab or a hospital. These angiography images may be acquired at the same time as a set of OCT or ultrasound images that are stored on the server 135. Simultaneous acquisition of angiography images and OCT or ultrasound images is feasible with the use of a radiopaque contrast fluid flush during invasive OCT or ultrasound imaging. A software algorithm executing on the server 135 or another component of the data collection system can be used to spatially co-register the angiography and the OCT or ultrasound data.

The hardware used to handle transmission of collected patient image data and to interface between different data collection systems or modules thereof can be configured in various ways. For example, software configured to process differ types of image data such as to co-register angiography and OCT and/or ultrasound data can receive data from the different components described herein. In one embodiment, optical data generated using OCT and acoustic data generated using IVUS can be combined individually or collectively with angiography data generated using x-rays wherein each of these three types of data are transmitted over one or more networks. Ultrasound data and angiography data can be transformed into optical signals and transmitted over one or more lengths of optical fibers used in some of the data collection systems described herein. As a result, in one embodiment, the invention relates to collecting a plurality of sets of image data using different imaging modalities and transmitting them over a network. This network or individual optical or electronic transmission paths can be integrated as part of a data collection system over one or more optical fibers in optical communication with a sample arm and/or a reference arm of an interferometer.

Figure 10B:
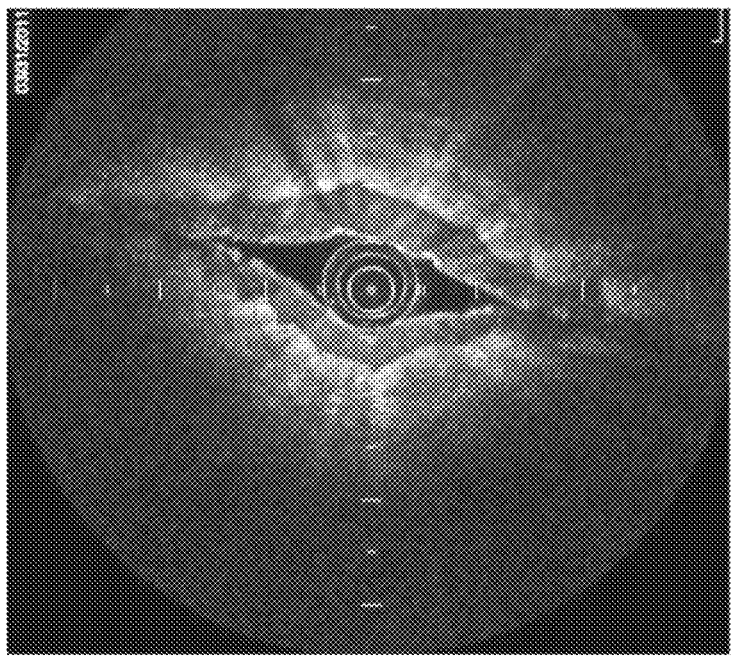
FIG. 10B depicts an ultrasound image of an OCT image of a living human finger pad using an embodiment of the invention.
Figure 10A:
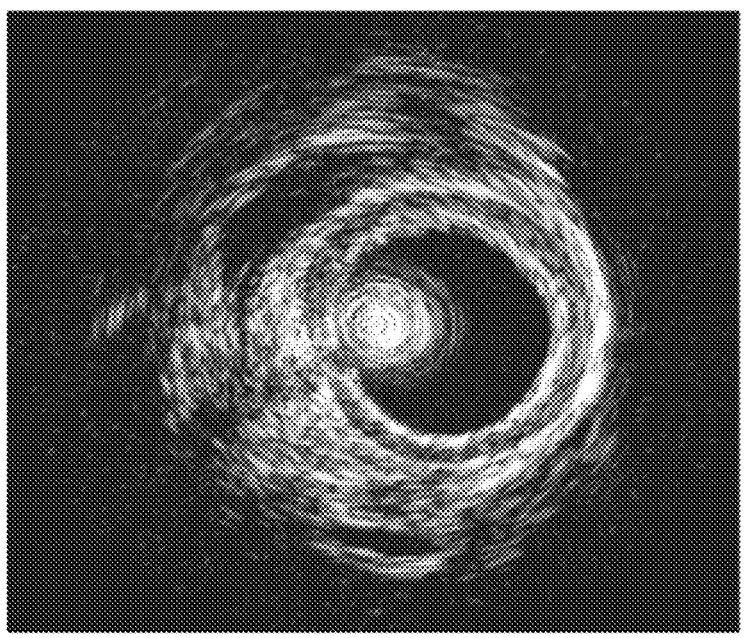
FIG. 10A depicts an ultrasound image of a fixed human coronary artery obtained using an embodiment of the invention.

FIGS. 10A and 10B show an ultrasound image of a fixed human coronary artery and an OCT image of a living human finger pad, respectively. The ultrasound image of FIG. 10A was acquired at a speed of 50,000 image lines per second and 100 frames per second, and was transmitted from a receiver to a digitizer board over a 15 meter single-mode optical fiber link. The OCT image of FIG. 10B was acquired at a speed of 100,000 image lines per second and 100 frames per second using the interferometer design described above. Sample arm and reference arm light was transmitted from the imaging engine to the PIU dock over 30 meter single-mode optical fiber links. Thus, it is possible and often desirable to separate certain components of a data collection system or a multimodal system using optical fiber links in various embodiments of the invention. Given the expense and size associated with a digitizer and the associated housing and controls that may be associated with the same, having a digitizer in one room such that it receives data from one or more procedure rooms is more efficient than having a digitizer in each room. The same can be said of the imaging engine and other components of a given data collection system described herein.

Accordingly, the angiography, OCT, and ultrasound data may be displayed together on the same monitor, and a marker may be placed on images formed from one modality to indicate the position of images formed from the other modality. For example, a marker may be placed on a 2D planar angiography image to indicate the position of a 2D cross-sectional OCT image acquired as part of a longer OCT pullback. This enables the operator to precisely assess on angiography the location of intravascular features visible only under OCT or IVUS. In this way, precise guidance of interventional procedures such as stent implantation is made possible.

In addition, embodiments of the invention relate to methods, systems, and devices that are suitable for efficiently allocating components of an OCT, IVUS, FFR or a multimodal system that combine two of the foregoing or other modalities into a system positioned at specific or general spatial coordinates relative to other components, devices or subsystems in a catheterization laboratory or cath lab or other medical facility. Thus, for example, in the context of an OCT system, a light source such as a swept laser, a digitizer, optical delay lines or fiber loops, interferometers and components thereof such as sample arms and reference arms, consoles, electrical subsystems and clock generators, housings for the foregoing and other items may be in optical or electrical communication with each other. Given that several of these constituents of an OCT system are bulky, expensive, fragile, sensitive to vibration or interference and/or possibly each of the foregoing, it is desirable to develop arrangements of such primary components or constituent elements that avoid unnecessary duplication, inefficiency, and reduced data quality.

In light of the foregoing, it is also worth noting that in many OCT, IVUS, and/or FFR data collection sessions; the procedure room in which the data is collected is adjacent to a dedicated control room. In one embodiment, individual carts or installations of an OCT system that include all of the necessary optical and electrical components can be used in a given procedure room. However, given the points raised above, a one-to-many topology that segregates some of the more expensive, heavier or bulky components as primary components from other parts of the system, secondary or $2^{nd}$ components, can reduce costs by having only one of each of the expensive, bulky, or delicate components connected to many procedure rooms.

Figure 11A:
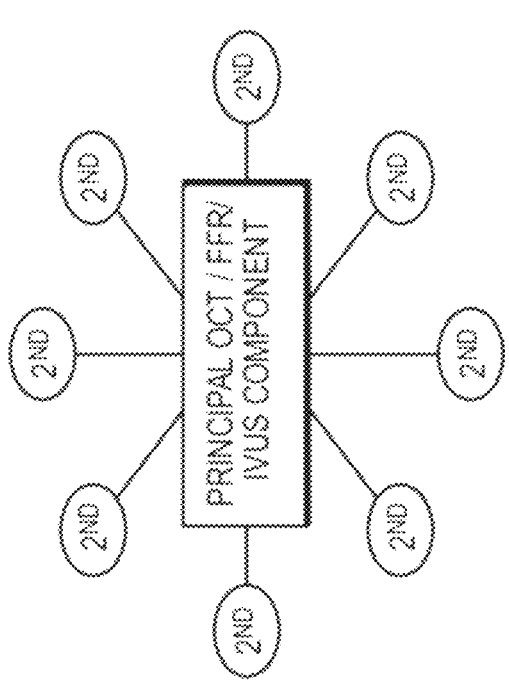
FIGS. 11A-11C depict various exemplary non-limiting topologies by which a principal OCT, IVUS, FFR or multimodal component is in communication with a one or more secondary OCT, IVUS, FFR or multimodal components.
Figure 11B:
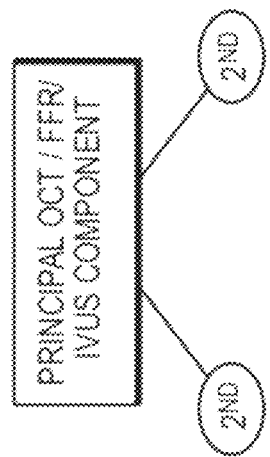
Figure 11C:
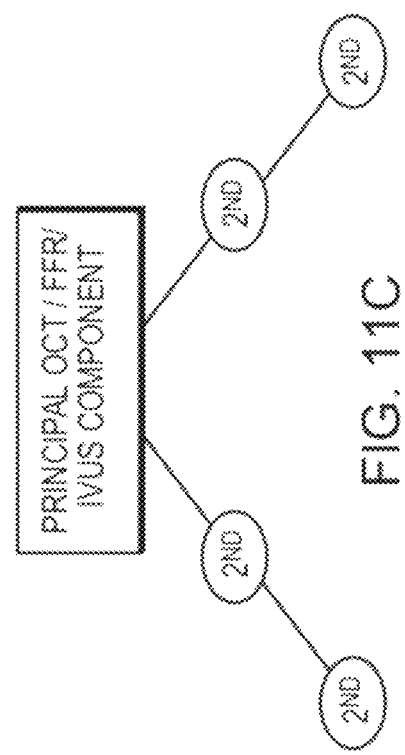

Thus, in one embodiment, a first data collection system such as an OCT, an IVUS, and/or a FFR system or a system that combines two or more of the foregoing can be configured such that its components are connected to form one or more networks. These configurations can be used to support the co-registration and transmission of ultrasound data or angiographic data along an optical fiber following a transformation from the format that the data was first collected, such as an acoustic signal or an electrical signal. Alternatively, electrical signal-based networks or sub-networks in communication with optical networks can be used. Various components of a data collection system such as a digitizer, a light source, a housing, or other OCT, IVUS, or FFR components can be identified as a principal component or node in a network that is either in electrical communication, optical communication, or both with a secondary OCT, IVUS, or FFR system component or a plurality of other or secondary OCT, IVUS, or FFR system components. The use of the terms primary and secondary is general and the various data collection systems and components thereof can be used without limitation regarding any of the components described herein. Examples of this are shown in FIGS. 11A-11C in which a primary component is electrically and/or optically coupled with a secondary component identified as "$2^{nd}$." Thus, in one embodiment, a digitizer and/or a light source or server can be a primary component that is at a first location.

As a result, the primary component is in electrical and/or optical communication with one or more secondary components. The primary and secondary components can include, without limitation, an OCT probe or part of the sample arm, pressure probe, wireless receiver, wireless transmitter, electro-optical signal converter, or other components. In turn, primary and secondary components can be positioned at different distances or different locations relative to each other. For example, these components can be positioned such that they are remote or proximal relative to a location such as a bed or as other location in a room. In one embodiment, components can be in the same room but still be remote from each other although linked by a length of optical fiber, an electrical wire or wireless connection. Thus, a patient can be resting on a support such as a bed during a data collection procedure such that, in one embodiment, the probe inserted in the patient's artery is a combination OCT and IVUS probe. The IVUS data can be generated acoustically and transmitted wirelessly to a receiver before being transmitted in an optical format following a transformation with an electro-optical converter. The optical OCT data and the IVUS data can be processed at a server to create a three-dimensional image or co-registered with angiography data or various other uses. These various steps and the devices used at each stage are configured to form a network of data processing and routing such that multi-room and remote in-room data collection and processing can be performed.

In one embodiment, the principal OCT component and the one or more secondary OCT components are in different rooms such as a control room or a procedure room. In one embodiment, the network topology by which the principal OCT component is in communication with one or more secondary OCT components can include, without limitation, a star topology, an extended star topology, a bus topology, a hierarchical topology, and other topologies that improve the cost to benefit ratio or signal to noise ratio for one or more OCT data collection sessions, either alone or in the aggregate.

Wireless Control Device

Figure 12:
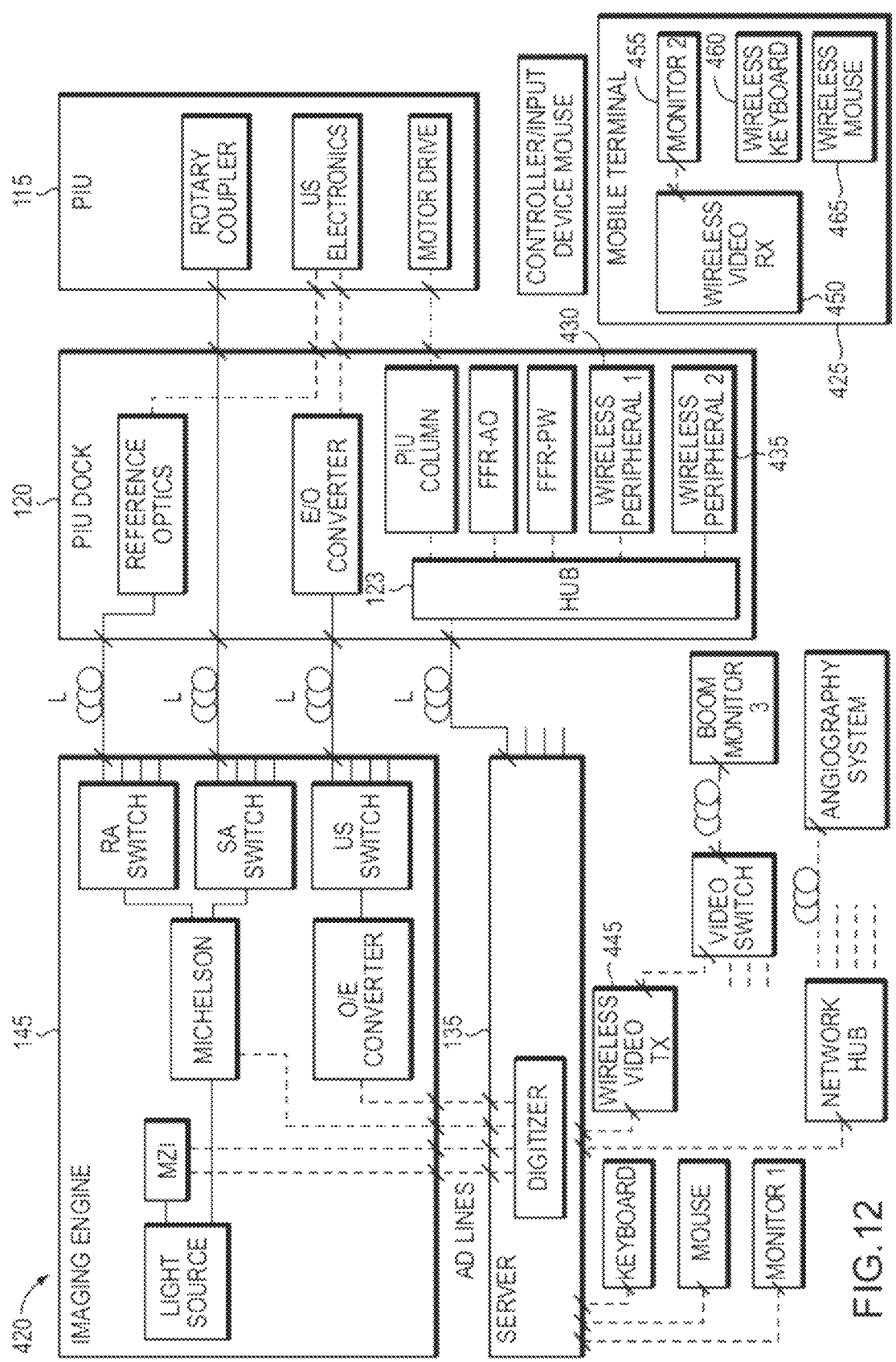
FIG. 12 is a schematic diagram of a system showing a wireless mouse or controller and a mobile terminal in accordance with an illustrative embodiment of the invention.

In one embodiment, the invention relates to an input device or controller configured to move in three-dimensions and control or display data collected with respect to a sample using one of the systems, devices or probes described herein. The input device or controller can be implemented as a mouse such as a tableside mouse, or a joystick such as a tableside joystick. A multimodal system 420, which has several elements in common with the embodiment of FIG. 1C include a mobile terminal 425 and various related mobile or wireless components. The bottom right quadrant of FIG. 12 shows such a controller or input device. The input device can translate a rotation or turn of the device into a wireless signal that can control what is displayed on a screen or remote terminal.

In one embodiment, the input device is a mouse or joystick such as the mouse shown in FIG. 12. Thus, in a mouse or joystick configuration, the input device is a pointing-and-clicking device that can be used in two modes. In the first mode, it is used as a wireless mouse or joystick in conjunction with a mouse tray or joystick enclosure box mounted to the bedside rail or another surface. In this mode, an optical sensor on the bottom of the mouse is used to track motion over the mouse tray, or a sensor or set of sensors in the joystick is used to track angular motion. The input device may be placed in a disposable sterile bag to prevent contamination, or the entire input device and tray may be draped in a sterile sheet for the same purpose.

In the second mode, the input device may be picked up off the mouse tray or other surface and used as a free-space pointer. The input device incorporates a set of gyroscopes or accelerometers to track motion in free space without requiring the use of a tray. Again, the input device may be placed in a disposable sterile bag to prevent contamination.

In both modes of operation, position data from the tableside mouse or joystick is transmitted to a first wireless transceiver located in a PIU dock that is also mounted to the patient table. The receiver can be a wireless USB dongle, and can be connected to a USB hub inside the PIU dock. A single USB connection to the server PC allows mouse commands to be implemented on the data collection system software. This USB connection may be a USB cable or an extended-length cable, depending on the distance between the PIU dock and the server PC. When the link length extends beyond several meters, an optical USB link may be used to prevent signal degradation and eliminate RF interference.

Figure 15:
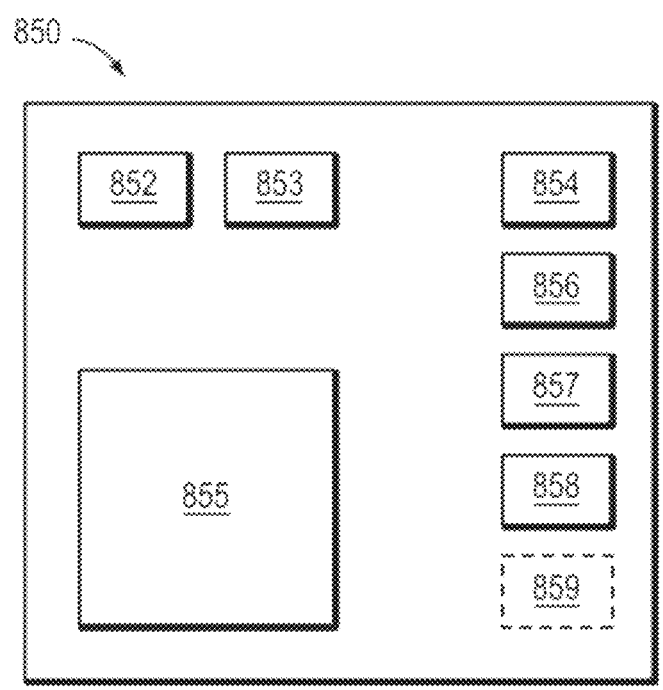
FIG. 15 is a schematic diagram of a probe and data collection system components accordance with an illustrative embodiment of the invention.
Figure 16:
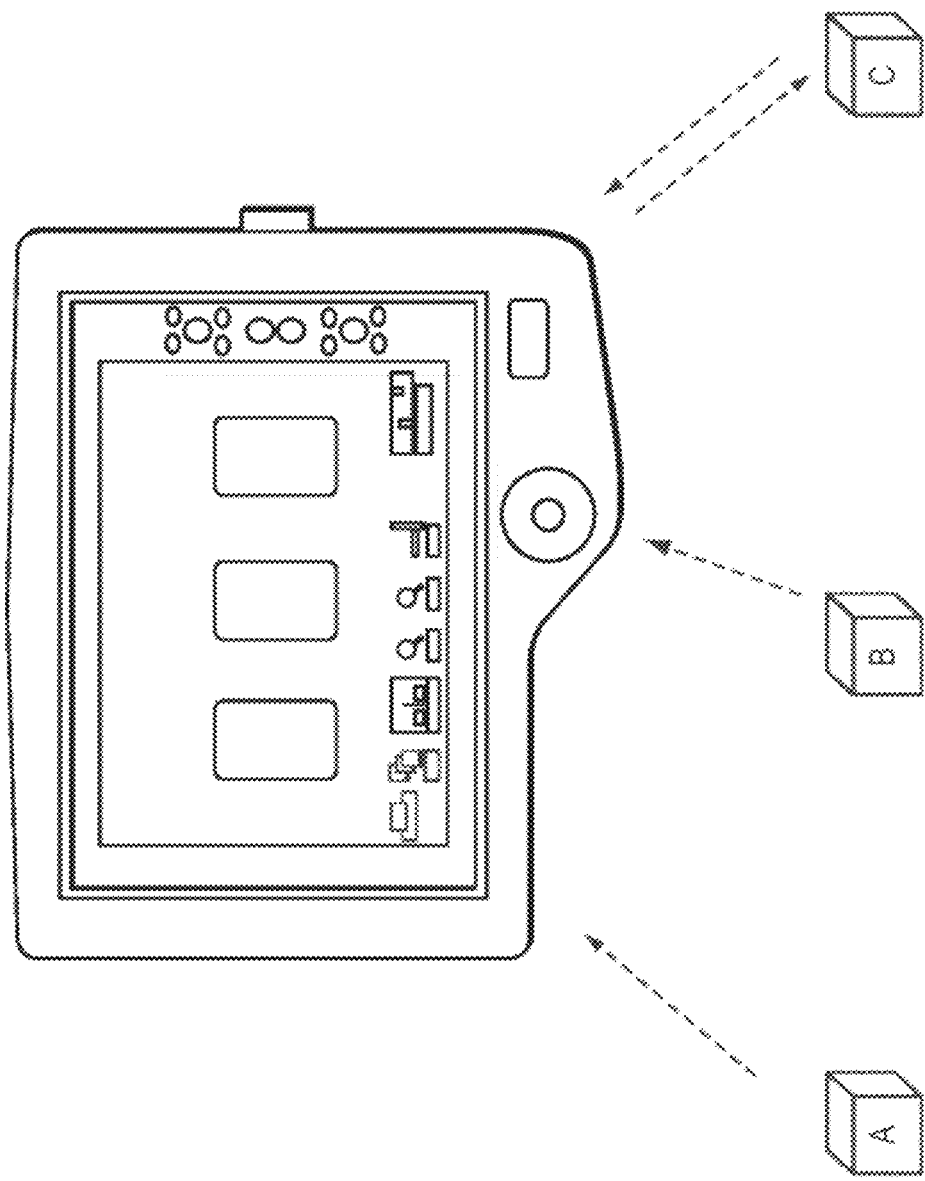
FIG. 16 is a schematic diagram of a data collection system and a graphic user interface in accordance with an illustrative embodiment of the invention.
Figure 17:
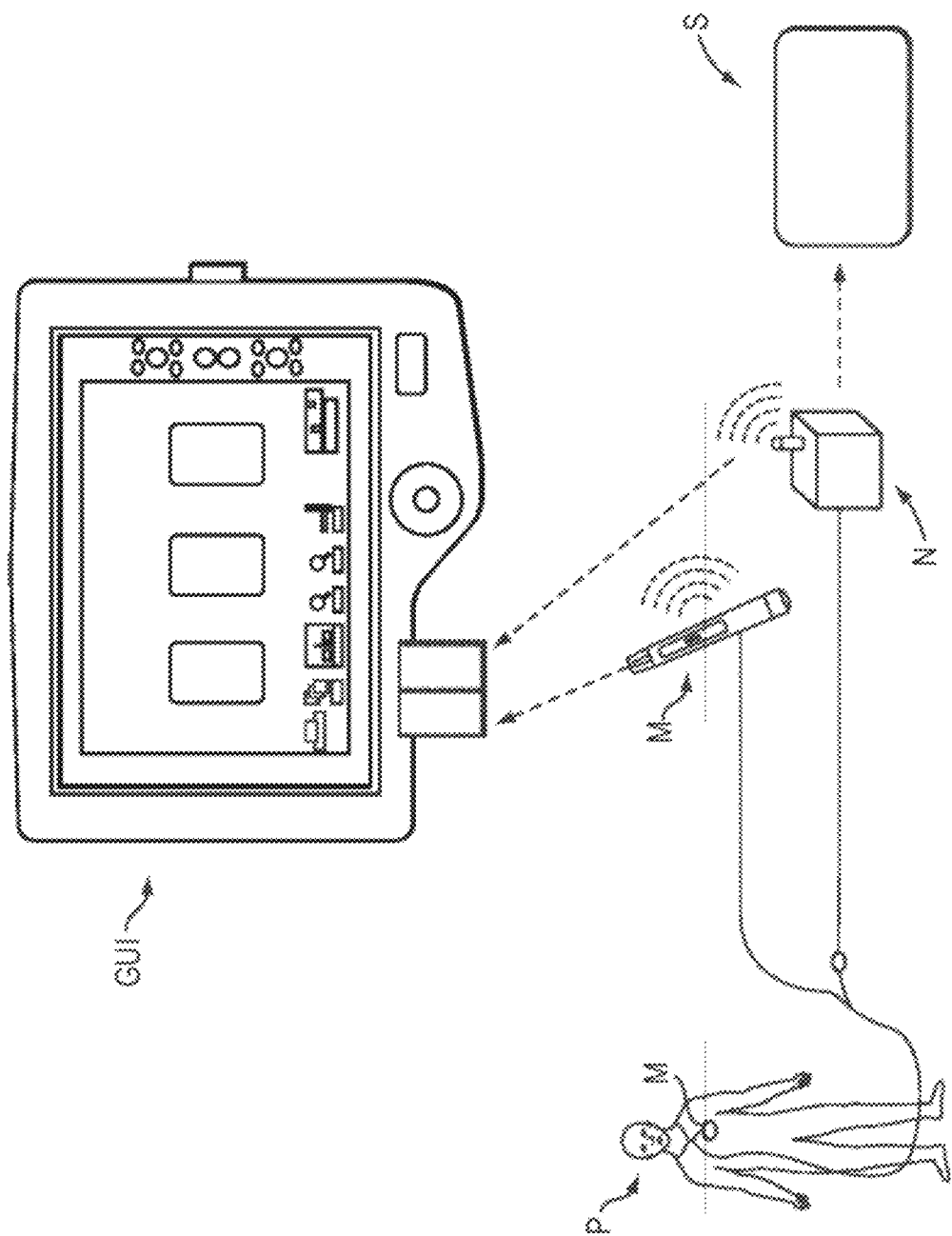
FIG. 17 is a schematic diagram of an input device or controller in accordance with an illustrative embodiment of the invention.

The mouse or joystick can be used by a clinician to control the data collection system or other components in electrical or optical communication therewith. Information from the data collection system, such as the systems in FIGS. 1A-1C, is displayed on an output device. The output devices can be a monitor mounted to a ceiling boom adjacent to the patient table. Other output device and/or related displays or interface subsystems suitable for use with input device are shown in FIGS. 15-17. The clinician may therefore be up to several meters away from the monitor or other output device while using the input device, such as a tableside mouse or joystick to operate the data collection system. For this reason, the graphical user interface (GUI) on the data collection system is modified with larger control buttons, dialog boxes, and text sizes. This GUI modification reduces the precision required from the mouse or joystick, making free-space pointer operation practical with a distant monitor.

In one embodiment, the input device can be translated in one direction to move along the path of a vessel rendered as a two-dimensional or three-dimensional tomographic image associated with an OCT data collection session such as a pullback. In one embodiment, rotating or otherwise translating the input device can cause a rotation of the 2D or 3D image of a vessel or components thereof. Pitch, yaw, angular position, x, y, and z positions can also be used to track movement of the input device wherein such movement causes images or other data to be displayed based on OCT, FFR, X-ray and other data for a given sample or patient of interest.

Mobile Terminal

In some situations, users prefer to control the data collection system from a location other than the patient bed or the control room. FIG. 12 shows an exemplary mobile terminal embodiment in the bottom right quadrant. A technician may, for example, prefer to control data acquisition and perform data review from a terminal in the procedure room. A mobile terminal using wireless communication addresses this need. The mobile terminal includes a wireless video receiver, monitor, wireless keyboard, and wireless mouse to control the data collection system or system in electrical or optical communication with it. The terminal can be mounted on a wheeled cart to allow it to be positioned anywhere in the procedure room. Other mobile devices can be used.

The wireless keyboard and mouse in the mobile terminal are in communication with a second wireless transceiver located in the PIU dock. This transceiver is connected to the same digital hub as the first wireless transceiver. The monitor on the mobile terminal receives video data from a wireless video receiver. This receiver is in communication with a wireless video transmitter connected to the server PC. The transmitter can be mounted in a location in or near the control room that allows the video signal to pass to the receiver without being affected by the radiation shielding commonly used in control room walls and windows.

In one embodiment, the data collection systems described herein includes a wired/wireless architecture that includes wired/wireless probes and control points. In addition, in one embodiment, the invention includes a wired/wireless touch screen control panel that can be used to operate a data collection system. The touch panel can include image display and interface functions. The mobile terminal can be configured to work in conjunction with a controller that transforms movements in three-dimensions to change an output on a display.

Medical Devices/Probes, Methods, and Other Features

One or more pressure probes can be used with the multimodal system described herein. These probes can include a pressure sensor or transducer that receives electrical power. To power a sensor positioned on or near a guidewire and to communicate signals representing a measured physiological variable to a control unit acting as an interface device disposed outside the body, one or more cables for transmitting the signals are connected to the sensor, and are routed along the guide wire to be passed out from the vessel to an external control unit via a connector assembly. The control unit may be adapted to convert sensor signals into a format accepted by the ANSI/AAMI BP22-1994. In addition, the guide wire is typically provided with a central metal wire (core wire) serving as a support for the sensor.

Figure 13:
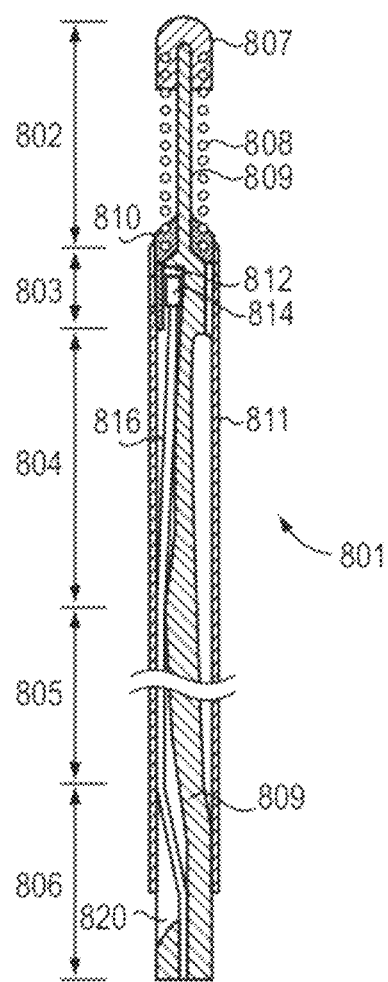
FIG. 13 is a schematic diagram showing a longitudinal view of a probe in accordance with an illustrative embodiment of the invention.

FIG. 13 shows a probe embodiment 801. The probe 801 includes a sensor and a guide wire. The probe has, in the drawing, been divided into five sections, 802-806, for illustrative purposes. The section 802 is the most distal portion, i.e. that portion which is going to be inserted farthest into the vessel, and section 806 is the most proximal portion, i.e. that portion being situated closest to a not shown control unit. Section 802 can include a radiopaque coil 808 made of e.g. platinum, provided with an arced tip 807. In the platinum coil and the tip, there is also attached a stainless, solid metal wire 809, which in section 802 is formed like a thin conical tip and functions as a security thread for the platinum coil 808. The successive tapering of the metal wire 809 in section 802 towards the arced tip 807 results in that the front portion of the sensor guide construction becomes successively softer.

At the transition between the sections 802 and 803, the lower end of the coil 808 is attached to the wire 809 with glue or alternatively, solder, thereby forming a joint 118. At the joint 118 a thin outer tube 811 commences which is made of a biocompatible material, e.g. polyimide, and extends downwards all the way to section 806. The tube 811 can be treated to give the sensor guide construction a smooth outer surface with low friction. The metal wire 809 is heavily expanded in section 803 and is in this expansion provided with a slot 812 in which a sensor element 814 is arranged, e.g. a pressure gauge. The sensor requires electric energy for its operation. The expansion of the metal wire 809 in which the sensor element 814 is attached decreases the stress exerted on the sensor element 814 in sharp vessel bends.

From the sensor element 814 there is arranged a signal transmitting cable 816, which typically can include one or more electric cables. The signal transmitting cable 816 extends from the sensor element 814 to an (not shown) interface device being situated below the section 806 and outside the body. A supply voltage is fed to the sensor via the transmitting cable 816 (or cables). The signals representing the measured physiological variable are also transferred along the transmitting cable 816. The metal wire 809 is substantially thinner in the beginning of section 804 to obtain good flexibility of the front portion of the sensor guide construction. At the end of section 804 and in the whole of section 805, the metal wire 809 is thicker in order to make it easier to push the sensor guide construction 801 forward in the vessel. In section 806 the metal wire 809 is as coarse as possible to be easy to handle and can include with a slot 820 in which the cable 816 is attached with e.g. glue.

Figure 14:
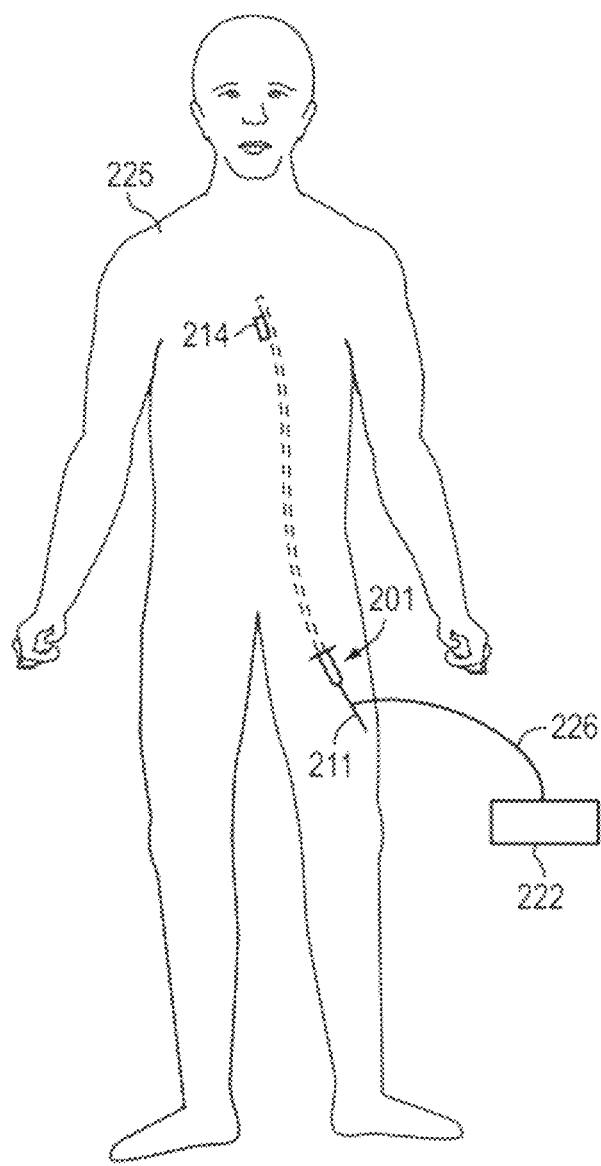
FIG. 14 is a schematic diagram of a patient with respect to which wireless measurements of FFR, image data, or other data can be obtained using systems and devices in accordance with an illustrative embodiment of the invention.

The use of a guide wire 201, such as is illustrated in FIG. 13, is schematically shown in FIG. 14. Guide wire 201 is inserted into the femoral artery of a patient 225. The position of guide wire 201 and the sensor 214 inside the body is illustrated with dotted lines. Guide wire 201, and more specifically electrically transmitting cable 211 thereof, is also coupled to a control unit 222 via a wire 226 that is connected to cable 211 using any suitable connector element or subsystem (not shown), such as a crocodile clip-type connector or any other known connector. The wire 226 is preferably made as short as possible for easiness in handling the guide wire 201. Preferably, the wire 226 is omitted, such that the control unit 222 is directly attached to the cable 211 via suitable connectors. The control unit 222 provides an electrical voltage to the circuit that includes wire 226, cable 211 of the guide wire 201 and the sensor 214. Moreover, the signal representing the measured physiological variable is transferred from the sensor 214 via the cable 211 to the control unit 222. The method to introduce the guide wire 201 is well known to those skilled in the art.

From the control unit 222, a signal representing distal pressure measured by the sensor 214 is communicated to one or more monitor devices, preferably using the ANSI/AAMI BP22-1994, either by means of wireless communication or via a wired connection. This information can be transmitted to one or more wireless pressure receivers such as receivers 129 and 130 of FIG. 1B.

The voltage provided to the sensor by the control unit could be an AC or a DC voltage. Generally, in the case of applying an AC voltage, the sensor is typically connected to a circuit that includes a rectifier that transforms the AC voltage to a DC voltage for driving the sensor selected to be sensitive to the physical parameter to be investigated.

FIG. 15 illustrates a data collection system 850 configured to use a medical device or probe, which can include a pressure or imaging component or subsystem for monitoring, analysing, and/or displaying physiological conditions or image data from within a body. The physiological conditions can include FFR, OCT image data, blood pressure, and other data collected using a probe or the systems of FIGS. 1A-1C.

The data collection system 850 can include a pressure wire receiver unit 852 configured to receive a wireless signal representing a measured physiological, or other, variable in the living body, an aortic blood pressure receiver unit 853 configured to receive, from at least one aortic pressure interface unit (not shown), a wireless signal including interface identity information required to identify the interface unit, and information representing measured aortic blood pressure. The system 850 can include a signal processing element or subsystem 854 configured to calculate blood pressure related parameters.

The system 850 can also include a touch screen 855 configured to display information regarding selectable aortic pressure interface units, pressure wire interface units, and blood pressure related parameters, FFR values, and OCT generated images, and to receive user input. In addition, the system 850 and an identifying unit 856 can be configured to identify interface units based upon received interface identity information, and a presentation unit 857 configured to present, on the touch screen 855, the interface unit(s) identified by the identifying unit 856. Furthermore, the system 850 can include selecting unit 858 configured to select one of the presented interface units. In one embodiment, the aortic blood pressure receiver unit 853 is configured to receive aortic pressure information from a selected aortic pressure interface unit. The touch screen 855 can include a graphic user interface suitable for selecting between rooms and data collections probes in the embodiments shown in FIGS. 1A-1C.

According to another embodiment of the invention, as shown in FIG. 15 by the dotted element, the probe 850 can further include a matching unit 859 that is configured to match identified interface units with a set of stored interface unit identities, and wherein the presentation unit 857 is configured to present, on the touch screen 855, the interface unit(s) having a positive match. In one embodiment, the selection by the selecting unit 858 is made in response of a user input on the touch screen 855. A pressure probe or pressure data receiver can have associated interface units configured to send data. The interface units can be probe interface units or interfaces or devices configured to transmit a particular type of data such as OCT, pressure, ultrasound, control signals, or other data.

In another embodiment, the selection by the selecting unit 858 is made automatically according to predetermined selecting rules. The predetermined selecting rules may include parameters related to the received wireless signal. For example, the predetermined selecting rules may include signal strength or an optical beam parameter. Accordingly, the selection by the selecting unit may be made by selecting the interface unit that has generated the wireless signal having the highest signal/noise ratio. The selection rule can also be reception of a trigger signal indicating which procedure room has a patient ready for an OCT pullback and image data collection event.

In one embodiment, the aortic blood pressure receiver unit 853 is configured to receive calibration data related to the selected aortic pressure interface unit. According to one embodiment, the pressure wire receiver unit 852 and/or the aortic blood pressure receiver unit 853 are detachable. In one embodiment, the pressure wire receiver unit is connectable to the device via a USB connection. In one embodiment, the aortic blood pressure receiver unit 853 is connectable to the device 850 via a USB connection or a wireless connection.

According to a further aspect, the invention relates to a medical system for monitoring, analysing, and displaying physiological conditions related to blood pressure within a living body, the system includes a probe, which can include a pressure or imaging probe. According to one embodiment of the invention, as illustrated in FIG. 16, the system for monitoring, analysing, and displaying physiological conditions or other data includes a display. As shown, the display of FIG. 16 can be fixed or mobile. A user interface and various inputs are included in the display device as shown. In one embodiment, the screen is a touch screen. Various data feeds or sources of physiological conditions or other data A, B, and C are shown. These can be any of the data generated or resulting from the processing of data generated by a data collection system such as those shown in FIGS. 1A-1C.

In turn, FIG. 17 shows a patient P to the left and a remote server or data collection S or processing system to the right. The patient P can be connected to various monitors or receivers (generally M) that collect local data such as blood pressure, oxygen levels, and others and relay such collected local data to one or more devices using a network device N having a wired connection, wireless or other connection. This data can be collected during an OCT or other catheter based procedure. In turn, once this data is captured, it can be wirelessly relayed to a display or a remote server or processing system S as shown. A handheld device or touchscreen monitor having a graphic user interface (GUI) can be used to control the system or collect data therefrom.

One embodiment of the invention can include one aortic pressure interface unit configured to receive information representing measured aortic blood pressure, and to transmit a wireless signal including interface identity information required to identify the interface unit, and information representing the measured aortic blood pressure.

One embodiment of the invention relates to a network of elements having electrical and optical inputs and outputs such that a mixed optical and electrical network of nodes and links results. In one embodiment, a link between two nodes that include either a principal OCT component and/or a secondary OCT component includes an arm of an interferometer such as a sample arm or a reference arm of an interferometer or a portion thereof.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The terms light and electromagnetic radiation are used interchangeably herein such that each term includes all wavelength (and frequency) ranges and individual wavelengths (and frequencies) in the electromagnetic spectrum. Similarly, the terms device and apparatus are also used interchangeably. In part, embodiments of the invention relate to or include, without limitation: sources of electromagnetic radiation and components thereof; systems, subsystems, and apparatuses that include such sources; mechanical, optical, electrical and other suitable devices that can be used as part of or in communication with the foregoing; and methods relating to each of the forgoing. Accordingly, a source of electromagnetic radiation can include any apparatus, matter, system, or combination of devices that emits, re-emits, transmits, radiates or otherwise generates light of one or more wavelengths or frequencies.

One example of a source of electromagnetic radiation is a laser. A laser is a device or system that produces or amplifies light by the process of stimulated emission of radiation. Although the types and variations in laser design are too extensive to recite and continue to evolve, some non-limiting examples of lasers suitable for use in embodiments of the invention can include tunable lasers (sometimes referred to as swept source lasers), superluminescent diodes, laser diodes, semiconductor lasers, mode-locked lasers, gas lasers, fiber lasers, solid-state lasers, waveguide lasers, laser amplifiers (sometimes referred to as optical amplifiers), laser oscillators, and amplified spontaneous emission lasers (sometimes referred to as mirrorless lasers or superradiant lasers).

Non-Limiting Software Embodiments for Multimodal Methods and Apparatus

The present invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In one embodiment of the present invention, some or all of the processing of the data collected using an OCT probe, ultrasound probe, FFR device, or other data collection modality is implemented as a set of computer program instructions that is converted into a computer executable form, stored as such in a computer readable medium, and executed by a microprocessor under the control of an operating system. Control and operation of components of a given component, system, subsystem, or apparatus can also be so controlled or operated using a computer. In one embodiment, light, radiofrequency, electrical and other signals or other data are transformed into processor understandable instructions suitable for collecting data from one or more modalities, triggering data collection or other clocking events, synchronizing data collection, transmitting data between one or more locations such as different rooms, and other features and embodiments as described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed over a network.

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, registering, co-registering, routing and processing instructions, or various types of data such as OCT scan data, ultrasound data, FFR data, interferometer signal data, clocks, radiofrequency data, and other information or data of interest.

Servers, computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

What is claimed is:

1. An image data collection system comprising:
   an interferometer comprising:
      a reference arm, wherein the reference arm receives light from a light source at a first location, wherein the reference arm terminates at a second location, an optical distance between the first location and the second location is L1, wherein the reference arm comprises a first optical fiber and
      a sample arm, wherein the sample arm receives light from the light source at the first location, wherein the sample arm terminates at a third location, the optical distance between the first location and the third location is L2, wherein the sample arm comprises a second optical fiber; and
   a first rotary coupler configured to interface with an optical coherence tomography imaging probe, wherein the first rotary coupler is in optical communication with the sample arm and wherein L2 and L1 are greater than 5 meters.

2. The system of claim 1 wherein the first optical fiber and the second optical fiber are both disposed in a common protective sheath.

3. The image data collection system of claim 2 wherein L1 and L2 and the disposition of the first optical fiber and the second optical fiber in the common protective sheath are configured to reduce degradation of an image formed using data collected by the optical coherence tomography imaging probe.

4. The image data collection system of claim 2 further comprising an electrically conductive wire disposed within the common protective sheath.

5. The image data collection system of claim 2 wherein the interferometer is installed in a first room and the rotary coupler is disposed in a second room and the length of the common protective sheath is sized to optically couple the first rotary coupler and the sample arm via the second optical fiber.

6. The image data collection system of claim 2 wherein the common protective sheath has a length greater than 5 meters and wherein a section of the reference arm and a section of the sample arm between an imaging engine and an interface dock are at least partially disposed within the protective sheath such that each section is exposed to similar environmental conditions.

7. The image data collection system of claim 2 further comprising one or more switches;
a server; and
one or more interface systems, each interface system in communication with a respective switch, each interface system configured to interface with the optical coherence tomography probe, a pressure wire or an ultrasound probe,
wherein the server is configured to collect data from each interface system, wherein each respective switch routes one or more signals.

8. The image data collection system of claim 7 further comprising:
an optical coupler having a first arm, a second arm and third arm, the first arm of the optical coupler in optical communication with the one or more switches;
a mirror in optical communication with the second arm of the optical coupler; and
a circulator having a first port, a second port and third port, the first port being in optical communication with the optical coupler, the second port in optical communication with a fiber Bragg grating, and a third port in optical communication with a photodetector,
wherein the photodetector generates a trigger signal when a wavelength occurs in the one or more signals.

9. The image data collection system of claim 7 wherein each interface system comprises an interface dock and an interface unit, wherein the interface dock provides an optical-electrical interface between the interface unit and the server.

10. The image data collection system of claim 2 further comprising a user interface device comprising a touch screen, a selecting unit configured to select between the optical coherence tomography imaging probe and a pressure transducer-based device, and a graphical user interface, the user interface device configured to display images generated using image data or a pressure data-based parameter and to receive user inputs.

11. The image data collection system of claim 10 wherein the user interface device is component of a mobile terminal in electrical or optical communication with a server configured to receive data from the optical coherence tomography imaging probe.

12. The image data collection system of claim 2 further comprising a variable path length air gap in optical communication with the reference arm.

13. The image data collection system of claim 1 further comprising an optical element configured to adjust a length of the reference arm, wherein the optical element is in optical communication with the reference arm and wherein the optical element is transmissive or reflective.

14. The image data collection system of claim 1 further comprising an ultrasound system comprising an electrical to optical converter configured to receive an electrical signal comprising ultrasound data and convert the electrical signal to an optical signal.

15. The image data collection system of claim 14 wherein the ultrasound system comprises a third optical fiber of length of L3, wherein the third optical fiber is configured to conduct the optical signal between a first location in which the interferometer is positioned and a second location in which the first rotary coupler is positioned, the third optical fiber having a first end and a second end.

16. The image data collection system of claim 15 further comprising a first wavelength division multiplexing filter in optical communication with the first end of the third optical fiber and a second wavelength division multiplexing filter in optical communication with the second end of the third optical fiber.

17. The image data collection system of claim 15 wherein the first optical fiber, the second optical fiber, and the third optical fiber and a strength member are all disposed in a common protective sheath.

18. The image data collection system of claim 14 further comprising a server configured to collect image data and a portable wireless control station comprising a display, and one or more input devices, wherein the portable wireless control station is configured to control at least one of the server and image data collection by the optical coherence tomography imaging probe.

19. The image data collection system of claim 18 wherein the server comprises a data acquisition device with two channels, wherein one channel is configured to acquire data according to a variable frequency external clock.

20. The image data collection system of claim 1 further comprising a circulator and a reflective or transmissive variable path length mirror in optical communication with the reference arm and the circulator.

21. The image data collection system of claim 1 further comprising a fiber Bragg grating and a photodetector, wherein the reference arm is in optical communication with the fiber Bragg grating and the photodetector.

22. The image data collection system of claim 21 wherein the photodetector is configured to transmit a pulse for synchronizing ultrasound data collection and OCT data collection in response to a received wavelength from the fiber Bragg grating.

23. The image data collection system of claim 1 wherein L2 is less than 30 meters.

24. The image data collection system of claim 23 wherein L1 is less than 30 meters.

* * * * *